United States Patent [19]

Brewer

[11] Patent Number: 5,543,499
[45] Date of Patent: Aug. 6, 1996

[54] DNA SEQUENCE ENCODING A POLYPEPTIDE WITH ANTI-TUMOR PROPERTIES

[75] Inventor: Gary Brewer, Winston-Salem, N.C.

[73] Assignee: Wake Forest University, Winston-Salem, N.C.

[21] Appl. No.: 146,421

[22] Filed: Oct. 29, 1993

[51] Int. Cl.[6] .............................. C07K 1/00; C07K 16/00; C12P 21/08
[52] U.S. Cl. .................... 530/350; 530/387.9; 530/388.1
[58] Field of Search ..................................... 530/350, 358, 530/387.9, 388.1; 514/12; 435/6

[56] References Cited

U.S. PATENT DOCUMENTS 5,354,847 10/1994 Liu et al. .............................. 530/387.3
5,444,149 8/1995 Keene et al. ............................. 530/300

OTHER PUBLICATIONS

Brewer Mol. and Cell Biol. vol. 11 pp. 2460–2466 May 1991.
Rasheed, et al. (1992) Genes, Chromosomes & Cancer 5:75–82.
Harris, et al. (1992) Blood 79(12):3316–3324.
Zhang, et al. (1993) Mol. Cell. Biol. 13(12):7652–7665.

*Primary Examiner*—Robert A. Wax
*Assistant Examiner*—Lisa J. Hobbs
*Attorney, Agent, or Firm*—Frederick W. Pepper

[57] ABSTRACT

The invention relates to the DNA sequence encoding the AUF1 polypeptide, or fragments thereof. Also, the invention relates to the AUF1 polypeptide itself or fragments thereof. Methods are disclosed for detecting the severity of neoplastic transformation. Methods are disclosed for detecting pharmacologicals that enhance the anti-tumor activity of AUF1. Methods are disclosed for treating a patient with a low level of the AUF1 gene.

4 Claims, 25 Drawing Sheets

Partial Sequences of RNA-Binding Substrates c-myc ARE

CAUCUUUUUUUUUCUUUAACAGAUUUGUAUUUAAGAAUUGUUUUUAAAAAAUU

UUAAGAUUUA c-fos ARE

UUUUAUUGUGUUUUUAAUUUAUUUAUUAAGAUGGAUUCUCAGAUAUUUAUAUU

UUUAUUUUAUUUUUUU

GM-CSF ARE

AUGGUGGGAGUGGCCUGGACCUGCCCUGGGCCACACUGACCCUGAUACAGGCAUG
GCAGAAGAAUGGGA<u>AUAUUUUAUACUGACAGAAAUCAGUAAUAUUUAUAU
AUUUAUAUUUUAAAAUAUUUAUUUAUUUAUUUAUUUAAGUUUCAUAUU</u>
CCAUAUUUAUUCAAGAUGUUUUACCGUAAUAAUUAUUAUUAAAAAUAUGCUUCUA

FIG. 2A ug of AUF-1 for immuno-absorption: 0, 0.05, 0.15, 0.5, 1.0 kD 45
40 -
37

```
GGAATTCCGG AATTCCGAAT GCGTCGGAAA GAGCGGGAGT GTGCGCCGCG CGAGAGTGGG

AGGCGAAGGG GGCAGGCCAG GGAGAGGCGC AGGAGCCTTT GCAGCCACGC GCGCGCGCTT

CCCTGTCTTG TGTGCTTCGC GAGGTAGAGC GGGCGCCGGC AGCGGCGGGG ATTACTTTGC

TGCTAGTTTC GGTTGCCGGC AGCGGCGGGT GTAGTCTCGG CGGCAGCGGC GGAGACACTA
```

```
GCACT ATG TCG GAG GAG CAG TTC GGC GGG GAC GGG GCG GCG GCA GCG
      Met Ser Glu Glu Gln Phe Gly Gly Asp Gly Ala Ala Ala Ala
      1             5                   10

GCA ACG GCG GCG GTA GGC GCT GCG GCG GGC GAG CAG GAG GGA GCC ATG
Ala Thr Ala Ala Val Gly Ala Ala Ala Gly Glu Gln Glu Gly Ala Met
15              20                  25                  30

GTG GCG GCG ACA CAG GGG GCA GCG GCG GCG CGG GAA GCG GAC GCG GGA
Val Ala Ala Thr Gln Gly Ala Ala Ala Ala Arg Glu Ala Asp Ala Gly
                35                  40                  45

CCG GGG GCG GAA CCG CGT CTG GAG GCA CCG AAG GGC AGC GCC GAG TCG
Pro Gly Ala Glu Pro Arg Leu Glu Ala Pro Lys Gly Ser Ala Glu Ser
            50                  55                  60

GAG GGG GCG AAG ATT GAC GCC AGT AAG AAC GAG GAG GAT GAA GGG AAA
Glu Gly Ala Lys Ile Asp Ala Ser Lys Asn Glu Glu Asp Glu Gly Lys
        65                  70                  75

ATG TTT ATA GGA GGC CTT AGC TGG GAC ACT ACA AAG AAA GAT CTG AAG
Met Phe Ile Gly Gly Leu Ser Trp Asp Thr Thr Lys Lys Asp Leu Lys
    80                  85                  90

GAC TAC TTT TCC AAA TTT GGT GAA GTT GTA GAC TGC ACT CTG AAG TTA
Asp Tyr Phe Ser Lys Phe Gly Glu Val Val Asp Cys Thr Leu Lys Leu
95                  100                 105                 110

GAT CCT ATC ACA GGG CGA TCA AGG GGT TTT GGC TTT GTG CTA TTT AAA
Asp Pro Ile Thr Gly Arg Ser Arg Gly Phe Gly Phe Val Leu Phe Lys
                115                 120                 125

GAA TCG GAG AGT GTA GAT AAG GTC ATG GAT CAA AAA GAA CAT AAA TTG
Glu Ser Glu Ser Val Asp Lys Val Met Asp Gln Lys Glu His Lys Leu
            130                 135                 140

AAT GGG AAG GTG ATT GAT CCT AAA AGG GCC AAA GCC ATG AAA ACA AAA
Asn Gly Lys Val Ile Asp Pro Lys Arg Ala Lys Ala Met Lys Thr Lys
        145                 150                 155

GAG CCG GTT AAA AAA ATT TTT GTT GGT GGC CTT TCT CCA GAT ACA CCT
Glu Pro Val Lys Lys Ile Phe Val Gly Gly Leu Ser Pro Asp Thr Pro
160                 165                 170
```

FIG. 8A

```
GAA GAG AAA ATA AGG GAG TAC TTT GGT GGT TTT GGT GAG GTG GAA TCC
Glu Glu Lys Ile Arg Glu Tyr Phe Gly Gly Phe Gly Glu Val Glu Ser
175             180             185             190

ATA GAG CTC CCC ATG GAC AAC AAG ACC AAT AAG AGG CGT GGG TTC TGC
Ile Glu Leu Pro Met Asp Asn Lys Thr Asn Lys Arg Arg Gly Phe Cys
                195             200             205

TTT ATT ACC TTT AAG GAA GAA GAA CCA GTG AAG AAG ATA ATG GAA AAG
Phe Ile Thr Phe Lys Glu Glu Glu Pro Val Lys Lys Ile Met Glu Lys
            210             215             220

AAA TAC CAC AAT GTT GGT CTT AGT AAA TGT GAA ATA AAA GTA GCC ATG
Lys Tyr His Asn Val Gly Leu Ser Lys Cys Glu Ile Lys Val Ala Met
        225             230             235

TCG AAG GAA CAA TAT CAG CAA CAG CAA CAG TGG GGA TCT AGA GGA GGA
Ser Lys Glu Gln Tyr Gln Gln Gln Gln Gln Trp Gly Ser Arg Gly Gly
    240             245             250

TTT GCA GGA AGA GCT CGT GGG GAA TTC CGG AAT TCC TCA GAG GCA GGA
Phe Ala Gly Arg Ala Arg Gly Glu Phe Arg Asn Ser Ser Glu Ala Gly
255             260             265             270

GAA GGC TTG GAG CTA CCC CCA AAC TCA ATC CAC TGT TGG CAG CTG AGC
Glu Gly Leu Glu Leu Pro Pro Asn Ser Ile His Cys Trp Gln Leu Ser
            275             280             285

GTG TAGTAGGGTG GTCCTAGCCA TACAGAACCA CTTCTCTGTC TCCCTCCTCT
Val

TCCCTGGTTC GTCCAGCCCC AGTCCATCAG GGACCACCTG GCAGCCTCC CAGAGATGGG

ATCGGGTTGG GGCTAAGGGC ATCGGGTCTG TCGCAGCCAG GGGTGCAGGA GGATCGCTGT

GCTGTGAGCC GTTCAGCTGG CTCCCGACGA AGGAGGCACG GAACCAGACA GCGCGGCGAG

GGCGAGAGCG CTGCAGGCAA GGCGTAGGCC CCGCGGCGGA TCTTGCCGAA GAGCAGGACA

GGCTCCGAGT CCTGGAAGGG GTAGTGGCCG GCCAGCATGG TGAAGAGCGC CACGCCCAGG

CTCCAGACAT CGGCTGCCTT GCCCGAGTAT GAGGCCCGTG AGCTGAGTAT CTCAGGTCCC

ACGTAGGCTG GCGACGCGTG CTTGTCCACA GGGAATCATC TGGCCCAGTC AGCACGCAGG

AGTCCTCCAG GTTCTCCAGC ACCAGCTTCT TCCTGGGACA TGGGGAGAAA CAGAAGGGTC

AGGTCCTACC CAGAACCCCC ATGCTATCAC CCTTGTGGCA CCCACTTTCC AAGTCGCTGC

TGGCCTTTGA CAGACACAAG CCAGTCCTGT GATGTCTGAT CCTGTTTTAC AGATACCCAA

GCCCAGGCTC AGAGAGGTTA AGTCATTTAA GGCCACAGAG CAATTAAATT TAAACTAAAA

TTCTGAAAGG AATACATTTT TCAACAGAGT CCTTGGGGAG GGGGCTGATG GGGCTGAGAG

GGTTAAGCCT CTCTTAAACC AGCTACAAAC TTAGGGTCCA GGCAGGTAAT AAGATGAGAG

AAACAGGAAG TGTGCCTGAC ATCTCAGCAC AAGCGCTACC TAAAAAGGGT ACACAACGCA

TTCTAGGGTT TACCAAGTGC CTGCTGTGTT CCTGGCCCTT GACCCAGCTC ATTACCTGGC

TCACCTCATT CTATCTAGCT ACAGCCTGCA AGGAAGACAC CATTTTACAG CTGTAGAGCA
```

FIG. 8B

```
TGGGCCTGGG ATGGGAACGC TGGCTGGCAG ATACTCAGAG CCAGTGCTGT GACCCACCCT

CTCAGTTCCC AAGATGGCCC CACATTCCCA TTGTTTTCCC AAGAGAAGC CAGGAATTGT

ATTTTAATGA AAAGGTCCCC ATTTAAAAAA TATTGGCAAA CCAGTTTATA TAAAAAACAC

AAACAGGTAA GCAGGGCAAA AAAAAAAGTG TGTAAGGCTG GCGCGGTGC TCATGCCCGG

TAATCCTAGC ACTTTGGGAG CGCGAGGCAG GGGGATCACT TGAGTTCAGG AGTTCAAGAC

CAGCCTGGGC AACACGGTAA AAACCTATCT CTACAAAAAA TACGAAAATT AGCAGGCATG

GTGATTCGCA CCTGTAGTCC CAGCTACTTG GGAGGCTGAT CTTGAACTCC TGAACTCAAG

TGATCCCCCT GCCTCGGCCG GAATTC
```

FIG. 8C

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:1:

```
CAUCUUUUUU UUUUCUUUAA CAGAUUUGUA UUUAAGAAUU GUUUUUAAAA AAUUUUAAGA          60

UUUA                                                                      64
```

( 2 ) INFORMATION FOR SEQ ID NO:2:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:2:

```
UUUUAUUGUG UUUUUAAUUU AUUUAUUAAG AUGGAUUCUC AGAUAUUUAU AUUUUUAUUU          60

UAUUUUUUU                                                                 69
```

( 2 ) INFORMATION FOR SEQ ID NO:3:

( i ) SEQUENCE CHARACTERISTICS:
        ( A ) LENGTH: 209 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:3:

```
AUGGUGGGAG UGGCCCUGGA CCUGCCCUGG GCCACACUGA CCCUGAUACA GGCAUGGCAG          60

AAGAAUGGGA AUAUUUAUA  CUGACAGAAA UCAGUAAUAU UUAUAUAUUU AUAUUUAAA          120

AUAUUUAUUU AUUUAUUUAU UUAAGUUUCA UAUUCCAUAU UUAUUCAAGA UGUUUUACCG          180

UAAUAAUUAU UAUUAAAAAU AUGCUUCUA                                           209
```

( 2 ) INFORMATION FOR SEQ ID NO:4:

( i ) SEQUENCE CHARACTERISTICS:
        ( A ) LENGTH: 2562 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 246..1106

( x i ) SEQUENCE DESCRIPTION: SEQ ID NO:4:

```
GGAATTCCGG AATTCCGAAT GCGTCGGAAA GAGCGGGAGT GTGCGCCGCG CGAGAGTGGG      60

AGGCGAAGGG GGCAGGCCAG GGAGAGGCGC AGGAGCCTTT GCAGCCACGC GCGCGCGCTT     120

CCCTGTCTTG TGTGCTTCGC GAGGTAGAGC GGGCGCCGGC AGCGGCGGGG ATTACTTTGC     180

TGCTAGTTTC GGTTGCCGGC AGCGGCGGGT GTAGTCTCGG CGGCAGCGGC GGAGACACTA     240

GCACT ATG TCG GAG GAG CAG TTC GGC GGG GAC GGG GCG GCG GCA GCG        287
      Met Ser Glu Glu Gln Phe Gly Gly Asp Gly Ala Ala Ala Ala
      1               5                   10

GCA ACG GCG GCG GTA GGC GCT GCG GCG GGC GAG CAG GAG GGA GCC ATG      335
Ala Thr Ala Ala Val Gly Ala Ala Ala Gly Glu Gln Glu Gly Ala Met
 15                  20                  25                  30

GTG GCG GCG ACA CAG GGG GCA GCG GCG GCG CGG GAA GCG GAC GCG GGA      383
Val Ala Ala Thr Gln Gly Ala Ala Ala Ala Arg Glu Ala Asp Ala Gly
                 35                  40                  45

CCG GGG GCG GAA CCG CGT CTG GAG GCA CCG AAG GGC AGC GCC GAG TCG      431
Pro Gly Ala Glu Pro Arg Leu Glu Ala Pro Lys Gly Ser Ala Glu Ser
             50                  55                  60

GAG GGG GCG AAG ATT GAC GCC AGT AAG AAC GAG GAG GAT GAA GGG AAA      479
Glu Gly Ala Lys Ile Asp Ala Ser Lys Asn Glu Glu Asp Glu Gly Lys
         65                  70                  75

ATG TTT ATA GGA GGC CTT AGC TGG GAC ACT ACA AAG AAA GAT CTG AAG      527
Met Phe Ile Gly Gly Leu Ser Trp Asp Thr Thr Lys Lys Asp Leu Lys
     80                  85                  90

GAC TAC TTT TCC AAA TTT GGT GAA GTT GTA GAC TGC ACT CTG AAG TTA      575
Asp Tyr Phe Ser Lys Phe Gly Glu Val Val Asp Cys Thr Leu Lys Leu
 95                 100                 105                 110

GAT CCT ATC ACA GGG CGA TCA AGG GGT TTT GGC TTT GTG CTA TTT AAA      623
Asp Pro Ile Thr Gly Arg Ser Arg Gly Phe Gly Phe Val Leu Phe Lys
                115                 120                 125

GAA TCG GAG AGT GTA GAT AAG GTC ATG GAT CAA AAA GAA CAT AAA TTG      671
Glu Ser Glu Ser Val Asp Lys Val Met Asp Gln Lys Glu His Lys Leu
            130                 135                 140

AAT GGG AAG GTG ATT GAT CCT AAA AGG GCC AAA GCC ATG AAA ACA AAA      719
Asn Gly Lys Val Ile Asp Pro Lys Arg Ala Lys Ala Met Lys Thr Lys
        145                 150                 155

GAG CCG GTT AAA AAA ATT TTT GTT GGT GGC CTT TCT CCA GAT ACA CCT      767
Glu Pro Val Lys Lys Ile Phe Val Gly Gly Leu Ser Pro Asp Thr Pro
160                 165                 170

GAA GAG AAA ATA AGG GAG TAC TTT GGT GGT TTT GGT GAG GTG GAA TCC      815
Glu Glu Lys Ile Arg Glu Tyr Phe Gly Gly Phe Gly Glu Val Glu Ser
175                 180                 185                 190

ATA GAG CTC CCC ATG GAC AAC AAG ACC AAT AAG AGG CGT GGG TTC TGC      863
Ile Glu Leu Pro Met Asp Asn Lys Thr Asn Lys Arg Arg Gly Phe Cys
                195                 200                 205

TTT ATT ACC TTT AAG GAA GAA GAA CCA GTG AAG AAG ATA ATG GAA AAG      911
Phe Ile Thr Phe Lys Glu Glu Glu Pro Val Lys Lys Ile Met Glu Lys
            210                 215                 220

AAA TAC CAC AAT GTT GGT CTT AGT AAA TGT GAA ATA AAA GTA GCC ATG      959
Lys Tyr His Asn Val Gly Leu Ser Lys Cys Glu Ile Lys Val Ala Met
        225                 230                 235

TCG AAG GAA CAA TAT CAG CAA CAG CAA CAG TGG GGA TCT AGA GGA GGA     1007
Ser Lys Glu Gln Tyr Gln Gln Gln Gln Gln Trp Gly Ser Arg Gly Gly
240                 245                 250

TTT GCA GGA AGA GCT CGT GGG GAA TTC CGG AAT TCC TCA GAG GCA GGA     1055
```

| Phe | Ala | Gly | Arg | Ala | Arg | Gly | Glu | Phe | Arg | Asn | Ser | Ser | Glu | Ala | Gly |
|---|---|---|---|---|---|---|---|---|---|---|---|---|---|---|---|
| 255 | | | | 260 | | | | | 265 | | | | | 270 | |

| GAA | GGC | TTG | GAG | CTA | CCC | CCA | AAC | TCA | ATC | CAC | TGT | TGG | CAG | CTG | AGC | 1103 |
|---|---|---|---|---|---|---|---|---|---|---|---|---|---|---|---|---|
| Glu | Gly | Leu | Glu | Leu | Pro | Pro | Asn | Ser | Ile | His | Cys | Trp | Gln | Leu | Ser | |
| | | | | 275 | | | | | 280 | | | | | 285 | | |

GTG TAGTAGGGTG GTCCTAGCCA TACAGAACCA CTTCTCTGTC TCCCTCCTCT 1156
Val

TCCCTGGTTC GTCCAGCCCC AGTCCATCAG GGACCACCTG GGCAGCCTCC CAGAGATGGG 1216

ATCGGGTTGG GGCTAAGGGC ATCGGGTCTG TCGCAGCCAG GGGTGCAGGA GGATCGCTGT 1276

GCTGTGAGCC GTTCAGCTGG CTCCCGACGA AGGAGGCACG GAACCAGACA GCGCGGCGAG 1336

GGCGAGAGCG CTGCAGGCAA GGCGTAGGCC CCGCGGCGGA TCTTGCCGAA GAGCAGGACA 1396

GGCTCCGAGT CCTGGAAGGG GTAGTGGCCG GCCAGCATGG TGAAGAGCGC CACGCCCAGG 1456

CTCCAGACAT CGGCTGCCTT GCCCGAGTAT GAGGCCCGTG AGCTGAGTAT CTCAGGTCCC 1516

ACGTAGGCTG GCGACGCGTG CTTGTCCACA GGGAATCATC TGGCCCAGTC AGCACGCAGG 1576

AGTCCTCCAG GTTCTCCAGC ACCAGCTTCT TCCTGGGACA TGGGGAGAAA CAGAAGGGTC 1636

AGGTCCTACC CAGAACCCCC ATGCTATCAC CCTTGTGGCA CCCACTTTCC AAGTCGCTGC 1696

TGGCCTTTGA CAGACACAAG CCAGTCCTGT GATGTCTGAT CCTGTTTTAC AGATACCCAA 1756

GCCCAGGCTC AGAGAGGTTA AGTCATTTAA GGCCACAGAG CAATTAAATT TAAACTAAAA 1816

TTCTGAAAGG AATACATTTT TCAACAGAGT CCTTGGGGAG GGGGCTGATG GGGCTGAGAG 1876

GGTTAAGCCT CTCTTAAACC AGCTACAAAC TTAGGGTCCA GGCAGGTAAT AAGATGAGAG 1936

AAACAGGAAG TGTGCCTGAC ATCTCAGCAC AAGCGCTACC TAAAAGGGT ACACAACGCA 1996

TTCTAGGGTT TACCAAGTGC CTGCTGTGTT CCTGGCCCTT GACCCAGCTC ATTACCTGGC 2056

TCACCTCATT CTATCTAGCT ACAGCCTGCA AGGAAGACAC CATTTTACAG CTGTAGAGCA 2116

TGGGCCTGGG ATGGGAACGC TGGCTGGCAG ATACTCAGAG CCAGTGCTGT GACCCACCCT 2176

CTCAGTTCCC AAGATGGCCC CACATTCCCA TTGTTTTCCC CAAGAGAAGC CAGGAATTGT 2236

ATTTTAATGA AAAGGTCCCC ATTTAAAAAA TATTGGCAAA CCAGTTTATA TAAAAAACAC 2296

AAACAGGTAA GCAGGGCAAA AAAAAAGTG TGTAAGGCTG GGCGCGGTGC TCATGCCCGG 2356

TAATCCTAGC ACTTTGGGAG CGCGAGGCAG GGGGATCACT TGAGTTCAGG AGTTCAAGAC 2416

CAGCCTGGGC AACACGGTAA AAACCTATCT CTACAAAAAA TACGAAAATT AGCAGGCATG 2476

GTGATTCGCA CCTGTAGTCC CAGCTACTTG GGAGGCTGAT CTTGAACTCC TGAACTCAAG 2536

TGATCCCCCT GCCTCGGCCG GAATTC 2562

( 2 ) INFORMATION FOR SEQ ID NO:5:

( i ) SEQUENCE CHARACTERISTICS:
        ( A ) LENGTH: 287 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Ser | Glu | Glu | Gln | Phe | Gly | Gly | Asp | Gly | Ala | Ala | Ala | Ala | Ala | Thr |
|---|---|---|---|---|---|---|---|---|---|---|---|---|---|---|---|
| 1 | | | | 5 | | | | | 10 | | | | | 15 | |

| Ala | Ala | Val | Gly | Ala | Ala | Ala | Gly | Glu | Gln | Glu | Gly | Ala | Met | Val | Ala |
|---|---|---|---|---|---|---|---|---|---|---|---|---|---|---|---|
| | | | 20 | | | | | 25 | | | | | 30 | | |

| Ala | Thr | Gln | Gly | Ala | Ala | Ala | Ala | Arg | Glu | Ala | Asp | Ala | Gly | Pro | Gly |
|---|---|---|---|---|---|---|---|---|---|---|---|---|---|---|---|
| | | 35 | | | | | 40 | | | | | 45 | | | |

| Ala | Glu | Pro | Arg | Leu | Glu | Ala | Pro | Lys | Gly | Ser | Ala | Glu | Ser | Glu | Gly |
|---|---|---|---|---|---|---|---|---|---|---|---|---|---|---|---|

|         | 50       |         |         |         | 55      |         |         |         | 60      |         |         |         |         |
|---------|----------|---------|---------|---------|---------|---------|---------|---------|---------|---------|---------|---------|---------|
| Ala 65  | Lys      | Ile     | Asp     | Ala     | Ser 70  | Lys     | Asn     | Glu     | Glu     | Asp 75  | Gly     | Lys     | Met Phe 80 |
| Ile     | Gly      | Gly     | Leu     | Ser 85  | Trp     | Asp     | Thr     | Thr     | Lys 90  | Lys     | Asp     | Leu     | Lys Asp Tyr 95 |
| Phe     | Ser      | Lys     | Phe 100 | Gly     | Glu     | Val     | Val     | Asp 105 | Cys     | Thr     | Leu     | Lys 110 | Leu Asp Pro |
| Ile     | Thr      | Gly 115 | Arg     | Ser     | Arg     | Gly 120 | Phe     | Gly     | Phe     | Val     | Leu 125 | Phe     | Lys Glu Ser |
| Glu     | Ser 130  | Val     | Asp     | Lys     | Val 135 | Met     | Asp     | Gln     | Lys     | Glu 140 | His     | Lys     | Leu Asn Gly |
| Lys 145 | Val      | Ile     | Asp     | Pro 150 | Lys     | Arg     | Ala     | Lys     | Ala 155 | Met     | Lys     | Thr     | Lys Glu Pro 160 |
| Val     | Lys      | Lys     | Ile     | Phe 165 | Val     | Gly     | Gly     | Leu     | Ser 170 | Pro     | Asp     | Thr     | Pro Glu Glu 175 |
| Lys     | Ile      | Arg     | Glu 180 | Tyr     | Phe     | Gly     | Gly     | Phe 185 | Gly     | Glu     | Val     | Glu 190 | Ser Ile Glu |
| Leu     | Pro      | Met 195 | Asp     | Asn     | Lys     | Thr     | Asn 200 | Lys     | Arg     | Arg     | Gly     | Phe 205 | Cys Phe Ile |
| Thr     | Phe 210  | Lys     | Glu     | Glu     | Glu     | Pro 215 | Val     | Lys     | Lys     | Ile     | Met 220 | Glu     | Lys Lys Tyr |
| His 225 | Asn      | Val     | Gly     | Leu     | Ser 230 | Lys     | Cys     | Glu     | Ile     | Lys 235 | Val     | Ala     | Met Ser Lys 240 |
| Glu     | Gln      | Tyr     | Gln     | Gln 245 | Gln     | Gln     | Gln     | Trp     | Gly 250 | Ser     | Arg     | Gly     | Gly Phe Ala 255 |
| Gly     | Arg      | Ala     | Arg 260 | Gly     | Glu     | Phe     | Arg     | Asn 265 | Ser     | Ser     | Glu     | Ala 270 | Gly Glu Gly |
| Leu     | Glu      | Leu 275 | Pro     | Pro     | Asn     | Ser     | Ile 280 | His     | Cys     | Trp     | Gln     | Leu 285 | Ser Val |

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Xaa  Gly  Phe  Xaa  Phe  Val  Xaa  Xaa
  1                        5

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Lys  Glu  Gln  Tyr  Gln  Gln  Gln  Gln  Gln  Trp  Gly  Ser  Arg  Gly  Gly
  1               5                       10                 15

( 2 ) INFORMATION FOR SEQ ID NO:8:

( i ) SEQUENCE CHARACTERISTICS:
        ( A ) LENGTH: 67 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:8:

```
CATCTTTTTT TTTTCTTTAA CAGATTTGTA TATAAGAATT GTTTTAAAA AATTTTAAGA,      60
TATACAC                                                                67
```

(2) INFORMATION FOR SEQ ID NO:9:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: mRNA (xi) SEQUENCE DESCRIPTION: SEQ ID NO:9:

```
AUUUAUUUAU UUAUUUA                                                     17
```

DNA SEQUENCE ENCODING A POLYPEPTIDE WITH ANTI-TUMOR PROPERTIES

The U.S. Government has a paid-up license in this invention and the right in limited circumstances to require the patent owner to license others on reasonable terms as provided for by the terms of Grant No. CA52443 awarded by the National Cancer Institute.

FIELD OF THE INVENTION

The present invention relates to the diagnostic and therapeutic uses of a cloned sequence of a gene which limits the expression of proto-oncogenes which, when overexpressed lead to cancer. More specifically, the invention relates to the tumor suppressor gene AUF1 and its expression product, a polypeptide which has anti-tumor properties.

BACKGROUND OF THE INVENTION

Tumor formation is often characterized by the uncoupling of the normally opposing processes of cellular proliferation and differentiation (Bishop, *Cell* 64:235–248 (1991); Hunter, *Cell* 64:249–270 (1991); and Sawyers et al., *Cell* 64:337–350 (1991)). The mechanisms that disrupt their normal coupling are believed to involve the overexpression or inappropriate expression of hematopoietic growth factors, growth factor receptors, and/or certain proto-oncogenes. The overexpression of the proto-oncogene c-myc has been detected in tumors, such as breast, stomach, lung, and colon carcinomas, neuroblastomas, and glioblastomas. Also, overexpression of c-myc induces neoplastic transformation of hematopoietic cells. For example, constitutive expression of the c-myc gene inhibits induced differentiation in erythroleukemia cells and in monocytic cells (Coppola and Cole, *Nature* 320:760–763 (1986)); Dmitrovsky et al., *Nature* 322:748–750 (1986); Larsson et al., *Proc. Natl. Acad. Sci. USA* 85:2638–2642 (1988); Prochownik and Kukowska, *Nature* 322:848–850 (1986)). Furthermore, antisense oligonucleotides to the c-myc coding region prevent accumulation of c-Myc protein. This results in maturation of the target hematopoietic cells (Holt et al., *Mol. Cell. Biol.* 8:963–973 (1988)). These studies support the hypothesis that the level of c-myc messenger RNA (mRNA) and protein sets the balance between proliferation and differentiation. Tuning c-myc to low levels allows for differentiation, while high levels favor proliferation. The deregulation of this balance appears to be one genetic event which can ultimately lead to the uncontrolled cell proliferation that is characteristic of the neoplastic phenotype.

The c-myc gene is not unique in terms of having an essential role in cellular growth processes. It has been known for decades that specific and timely changes in the expression of multiple genes are required for proper embryonic development and cell maturation (Davidson, *Gene Activity in Early Development*, 3rd ed., Academic Press, Orlando, Fla. (1986)). However, studies have focused on c-myc, because it seems to be regulated not only at the levels of transcription, attenuation, nuclear processing, and translation, but also at the level of mRNA turnover (Marcu et al., *Ann. Rev. Biochem.* 61:809–860 (1992)). Indeed, direct half-life measurements indicated that c-myc mRNA has a half-life of 15–40 minutes (Dani et al., *Proc Natl. Acad. Sci., USA* 81:7046–7050 (1984); Dani et al., *Proc. Natl. Acad. Sci., USA* 82:4896–4899 (1985) and Piechaczyk et al., *Cell* 42:597–598 (1985)). These and other studies (Marcu et al., Ibid.) demonstrated that the control of c-myc mRNA turnover might be an important means of regulating both the level and timing of c-myc expression.

Many proto-oncogene mRNAs are very unstable. The rapid turnover of c-myc mRNA is controlled by sequences in the 3'-untranslated region (3'UTR) or by coding region sequences (Laird-Offringa, *BioEssays* 14:119–124 (1992) and Schiavi et al., *Biochim. Biophy. Acta* 1114:95–106 (1992)). A common feature in the labile mRNAs of proto-oncogenes, such as c-myc, c-fos and of the cytokine GM-CSF, is the presence of an AU-rich element (ARE) in the 3'UTR which is one cis-acting element responsible for their rapid degradation (Atwater et al, *Annu. Rev. Genet.* 24:519–541 (1990); Peltz et al., *Crit. Rev. Euk. Gene Expression* 1:99–126 (1991) and Schiavi et al., *Biochim. Biophy. Acta* 1114: 95–106 (1992)).

Functionally, the ARE appears to mediate sequentially rapid deadenylation which is followed by cleavage of the body of the mRNA (Brewer and Ross, *Mol. Cell. Biol.* 8:1697–1708 (1988); Shyu et al., *Genes Dev.* 5:221–231 (1991); Wilson and Treisman, *Nature* 336:396–399 (1989)). Several groups have identified ARE-binding proteins that might mediate the degradation of these mRNAs (Bickel et al., *Proc. Natl., Acad. Sci. USA* 89:10001–10005 (1992); Bohjanen et al., *Mol. Cell. Biol.* 11:3288–3295 (1991); Bohjanen et al., *J. Biol. Chem.* 267:6302–6309 (1992); Brewer, *Mol. Cell. Biol.* 11:2460–2466 (1991); Malter, *Science* 246:664–666 (1989); Myer et al., *Proc. Natl. Acad. Sci. USA* 89:1296–1300 (1992); Vakalopoulou et al., *Mol. Cell. Biol.* 11:3355–3364 (1991); You et al., *Mol. Cell. Biol.* 12:2931–2940 (1992)). Recently, Hamilton et al., *J. Biol. Chem.* 268:8881–8887 (1993) identified two of these ARE-binding proteins as hnRNP A1 and C.

These ARE-binding proteins are capable of limiting the expression of proto-oncogenes whose overexpression activates the growth of cells found in malignant tumors. Therefore, the genes responsible for the expression of these ARE-binding proteins represent a new mechanism of tumor suppression, degrading proto-oncogene mRNAs to limit their expression. Previously, tumor suppressor genes were known only to encode proteins controlling transcription and translation. Only a limited number of tumor suppressor genes have been identified. To expand the number of therapeutic targets and diagnostic tools for cancer, additional tumor suppressor genes need to be identified.

SUMMARY OF THE INVENTION

The present invention provides a purified and isolated polypeptide product and fragments of the polypeptide capable of limiting the expression of a proto-oncogene. The particular polypeptide is AUF1. An AUF1 polypeptide fragment capable of limiting the expression of a proto-oncogene has an amino-terminal sequence beginning with amino-terminal amino acid residue 92 Asp and a carboxy-terminal residue extending no further than amino acid residue 287 Val. The invention also concerns the purified and isolated DNA sequence and fragments thereof, encoding the polypeptide product and fragments of the polypeptide. Correspondingly provided are monoclonal and polyclonal antibodies which are immunoreactive with such polypeptides. Further the invention concerns a composition containing AUF1 polypeptide, or a fragment thereof, in a pharmacologically acceptable carrier, suitable for treating a human having a low level of the AUF1 gene.

Another aspect of the invention involves the use of an isolated AUF1 gene to synthesize AUF1 polypeptide for use in the treatment of individuals determined to have a low level of the AUF1 gene.

In yet another aspect, the invention involves a method of detecting the degree of loss in a cell sample of a polypeptide such as AUF1 for determining the severity of neoplastic transformation. This involves generating an antibody to the polypeptide products of AUF1. Then contacting the antibody with the cell sample and detecting the amount of immune complex formation as an indication of the degree of loss of the AUF1 polypeptide in the cell sample. A lower amount of immune complex formulation, than found in a normal cell, indicates that the neoplastic transformation is caused by a less than normal amount of the AUF1 polypeptide as a result of a low level of the AUF1 gene. This procedure would preferably involve contacting a cell sample from a human patient with an antibody (e.g., monoclonal antibody) which specifically reacts with the AUF1 polypeptide, or a fragment thereof. Then determining the amount of immune complex formation present in the cell sample. A lower amount of immune complex formation, than found in a normal cell, indicates that the neoplastic transformation is caused by a less than normal amount of the AUF1 polypeptide as a result of a low level of the AUF1 gene. Also, using this procedure, a direct correlation can be made between a lower amount of immune complex formation and a greater severity of the neoplastic transformation.

Another method for determining the severity of neoplastic transformation is the use of probes that bind to the RNA of the AUF1 gene. This involves hybridizing an RNA extracted from a cell sample of a human patient with a probe specific for the AUF1 gene. Then determining the degree of hybridization to the mRNA as an indication of the degree of loss of the AUF1 gene in the cell sample. A lesser degree of hybridization, than found in a normal cell, indicates that the neoplastic transformation is caused by a less than normal amount of the AUF1 polypeptide as a result of a low level of the AUF1 gene. Also, a direct correlation can be made between a lesser degree of hybridization and a greater severity of the neoplastic transformation.

A further aspect of the invention involves a method for detecting a pharmacological that enhances the anti-tumor activity of a polypeptide such as AUF1 by increasing the binding affinity of the polypeptide for a proto-oncogene. This involves mixing the polypeptide, a radiolabeled ARE-RNA of the proto-oncogene, and the pharmacological. The resulting mixture is filtered through a membrane such as nitrocellulose. Pharmacological that enhance the anti-tumor activity of the polypeptide do so by increasing the binding affinity of the polypeptide for the ARE-RNA. Since the polypeptide binds to the membrane, the radiolabeled ARE-RNA complexed with the polypeptide will adhere by means of the polypeptide. Any increased binding affinity is reflected by the increased counts per minute (cpm) retained on the membrane reflecting the increased amount of bound radiolabeled ARE-RNA as a result of the presence of the pharmacological.

An additional aspect of the invention involves a method for detecting a pharmacological that regenerates cells of neural origin by decreasing the binding affinity of a polypeptide such as AUF1 for a proto-oncogene. This involves mixing the polypeptide, a radiolabeled ARE-RNA of the proto-oncogene, and the pharmacological. The resulting mixture is filtered through a membrane such as nitrocellulose. Pharmacological that regenerate cells of neural origin do so by decreasing the binding affinity of the polypeptide for the ARE-RNA. Since the polypeptide binds to the membrane, the radiolabeled ARE-RNA complexed with the polypeptide will adhere by means of the polypeptide. Any decreased binding affinity is reflected by the decreased counts per minute (cpm) retained on the membrane reflecting the decreased amount of bound radiolabeled ARE-RNA as a result of the presence of the pharmacological.

BRIEF DESCRIPTION OF THE DRAWINGS

FIG. 2A SEQ ID NO:1, SEQ ID NO:2, and SEQ ID NO:3 lists partial sequences of RNA-binding substrates containing ARE used in UV-crosslinking to AUF1;

FIGS. 3A, 3B, and 3C show Western blot analyses characterizing the anti-AUF1 polyclonal antibody;

FIGS. 8A, 8B, and 8C SEQ ID NO:4 represent the nucleotide sequence of the cloned cDNA and predicted amino acid sequence;

DETAILED DESCRIPTION OF THE INVENTION

Figure 1A:
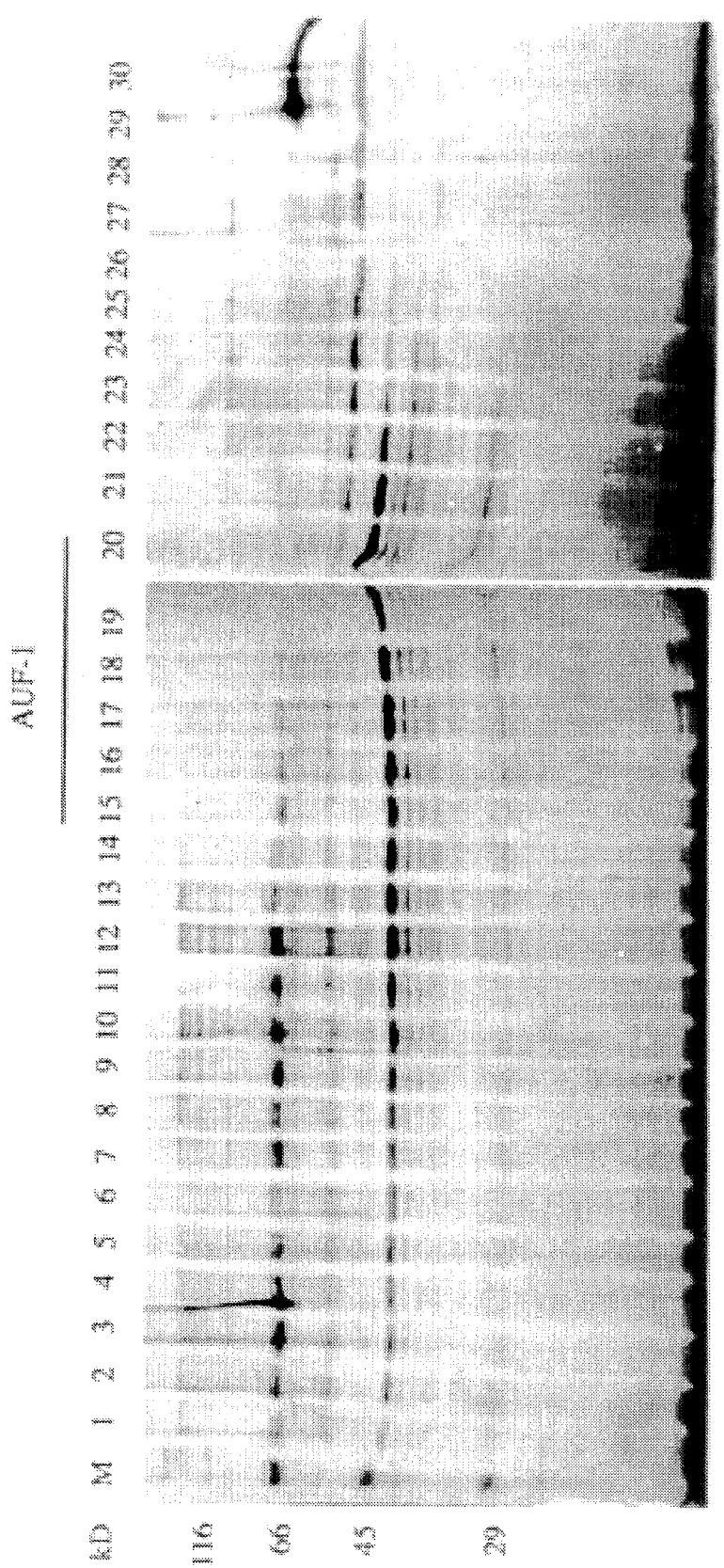
FIG. 1A represents a SDS-PAGE showing the polypeptide profile of AUF1 eluated from a poly(U)-agarose column.

The present invention provides a purified and isolated DNA sequence of a gene, AUF1, that encodes a purified and isolated polypeptide and fragments of the polypeptide which bind to the mRNA encoded by a proto-oncogene. The binding to the mRNA results in the mRNA's degradation and the loss of the encoded proto-oncogene protein. Therefore, the AUF1 polypeptide and fragments of the polypeptide encoded by the gene limit the expression of a proto-oncogene which, when overexpressed leads to cancer. The proto-oncogenes whose expression is limited by the AUF1 polypeptide include c-myc, c-myb, and c-fos.

Also provided by the present invention are synthetically produced polypeptides that have a biological activity of the AUF1 polypeptide produced from purified and isolated DNA sequences through an in vitro expression system. The fragments of the AUF1 polypeptide either have a biological activity of the naturally occurring AUF1 protein, or include an epitope of this polypeptide which enables them to produce AUF1 antibodies. The purified and isolated DNA sequence encoding the AUF1 polypeptide can be carried on vectors which can be propagated in cells. The purified and isolated DNA sequence encoding the AUF1 polypeptide is defined as a DNA sequence isolated from its natural environment (e.g., cDNA or genomic DNA) which hybridizes to the AUF1 gene under hybridizing conditions.

Purification and isolation of the recombinantly expressed polypeptide and polypeptide fragments may be obtained by conventional means, e.g., preparative chromatographic separations and immunological separations involving monoclonal and/or polyclonal antibody preparations. This represents an opportunity to provide significant amounts of the AUF1 polypeptide and its fragments for use in therapy, and to design suitable diagnostic tests to detect the presence of tumors in an organism.

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host used.

"Expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA. Clearly, a lack of replication would render them effectively inoperable. In sum, "expression vector" is also given a functional definition. Generally, expression vectors of utility in DNA recombinant techniques are often in the form of "plasmids". Plasmids refer to either circular double stranded DNA molecules or circular single stranded DNA molecules, containing an origin of replication derived from a filamentous bacteriophage. These DNA molecules, in their vector form, are not linked to the chromosomes. Other effective vectors commonly used are phage and non-circular DNA. In the present specification, "plasmid" and "vector" are often used interchangeably. However, the invention is intended to include such other forms of expression vectors which serve equivalent functions and which are, or subsequently become, known.

Recombinant vectors and methodology disclosed herein are suitable for use in a wide range of procaryotic and eucaryotic host cells. These host cells include microbial strains and cell lines derived from multicellular eucaryotic organisms.

"Recombinant host cells", "host cell", "cells", "cell cultures" and so forth are used interchangeably to designate individual cells, cell lines, cell cultures, and harvested cells which have been or are intended to be transformed or transfected with the recombinant vectors of the invention. The terms also include the progeny of the cells originally receiving the vector.

"Transformed" or "transfected" refers to any process for altering the DNA content of the host. This includes in vitro transformation procedures such as calcium phosphate or DEAE-dextran-mediated transfection, electroporation, nuclear injection, phage infection, or such other means for effecting controlled DNA uptake as are known in the art.

"S130" is a 130,000×g post-ribosomal supernatant of cell extracts, i.e., cytosol.

Isolation of AUF1

Figure 1B:
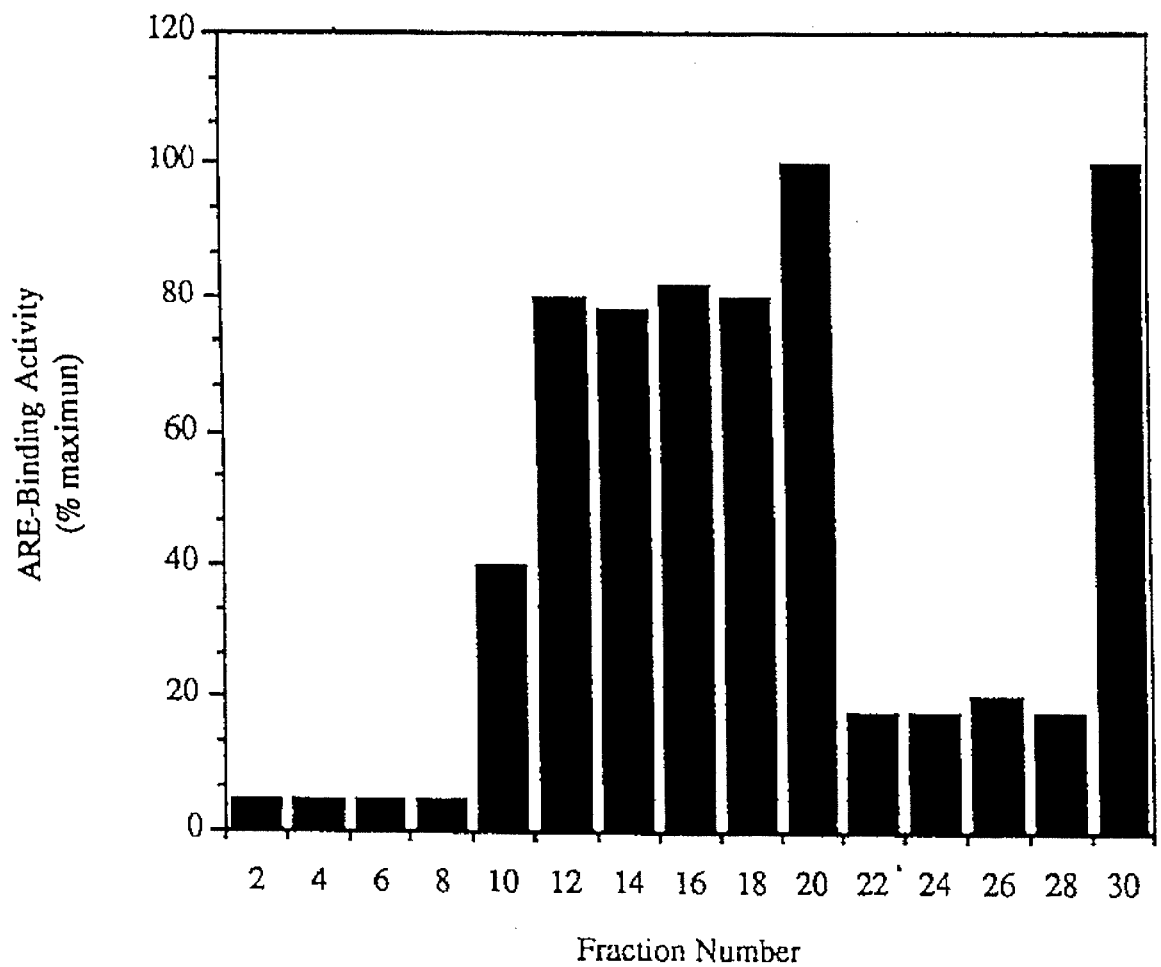
FIG. 1B is a bar graph showing the percent of maximum ARE RNA-binding activity of AUF1 eluate fractions.

Due to the affinity of the S130-associated ARE-binding activity for poly(U), S130 was fractioned by column chromatography using heparin-agarose followed by poly(U)-agarose (see Example 1). For the poly(U)-agarose step, a gradient of increasing potassium acetate concentration was used to elute bound polypeptides. RNA-binding activity was assayed by gel mobility shift using a nP-labeled region of the human c-myc 3'UTR containing the ARE (Brewer, *Mol. Cell. Biol.* 11:2460–2466 (1991)). The majority of a 40 kD polypeptide and a minor doublet of 36/37 kD eluted from the affinity matrix at 3.0–3.5M KOAc in fractions 12–20 (FIG. 1A). Maximal ARE-binding activity was also present in these fractions (FIG. 1B). This activity is referred to as AU-rich element RNA-binding factor-one or AUF1. The three polypeptides of 40 kD and 36/37 kD cofractionated using poly(U)-agarose chromatography (FIG. 1A), gel filtration using sephacryl S300 chromatography and C8 reverse-phase HPLC.

RNA-Binding Specificity of AUF1

Figure 2B:
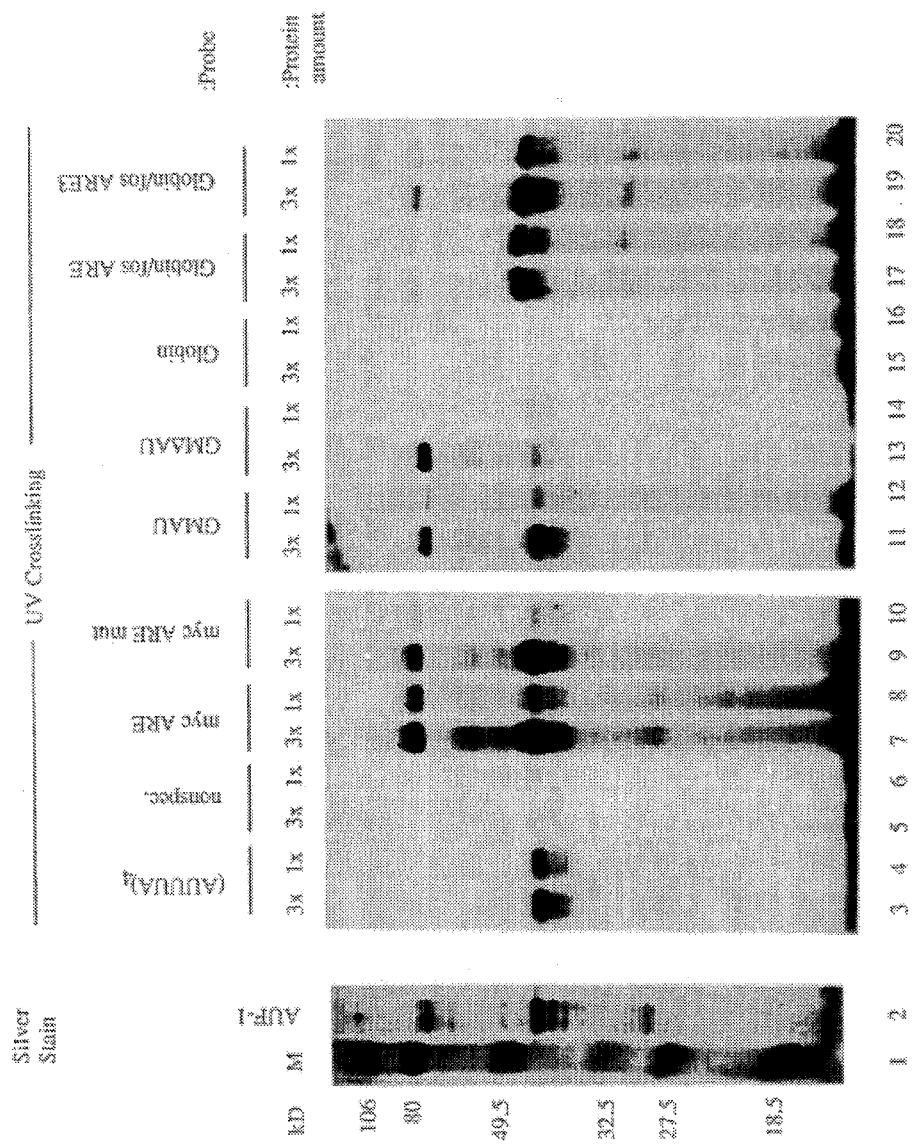
FIG. 2B represents an SDS-PAGE showing UV-crosslinking analysis of AUF1 to $^{32}$P-labeled RNA substrates.

The RNA-binding specificity of AUF1 was examined using RNA substrates containing AU-rich sequences shown by other groups to destabilize the mRNA (Schiavi et al., *Biochim. Biophy. Acta* 1114:95–106 (1992)). Fractions 15–20 from the poly(U)-agarose column (FIG. 1A) were pooled, dialyzed, concentrated and tested in UV-crosslinking assays. The poly(U)-agarose eluate was mixed with $^{32}$P-labeled RNA substrates. Partial sequences of selected target RNAs are shown in FIG. 2A SEQ ID NO.1, SEQ. ID NO:2, and SEQ ID NO:3. Following incubation to permit binding, the mixture was irradiated with 254 nm light then treated with RNase A. Crosslinked proteins were separated by SDS-PAGE and visualized by autoradiography (FIG. 2B). An adjacent lane on the gel was loaded with affinity-purified protein and silver-stained for comparison (FIG. 2B, lane 2). The major 40 kD species and minor 36/37 kD doublet crosslinked to the wild-type ARE-RNA substrates (FIG. 2B, lanes 3, 4, 7, 8, 11, 12, 17 and 18). RNA binding by polypeptides in the poly(U)-agarose eluate was also assessed by UV-crosslinking to substrates lacking intact AUUUA motifs. The 40 and 36/37 kD species did not detectably crosslink to RNA of random sequence or to β-globin (FIG. 2B, lanes 5, 6, 15 and 16). They crosslinked at 15% efficiency to GMAAU, the mutant GM-CSF 3'UTR lacking the 83 nt ARE, compared to wild-type GM-CSF ARE (FIG. 2B, compare lane 13 with lane 11). They also crosslinked to c-myc and c-fos ARE mutants lacking intact AUI/UA pentanucleotides (see FIG. 2A SEQ ID NO:1 SEQ ID NO:2, and SEQ ID NO:3; FIG. 2B, lanes 9, 10, 19 and 20). In this case the crosslinking efficiency was equivalent to that seen with wild-type ARE RNAs.

Figure 2C:
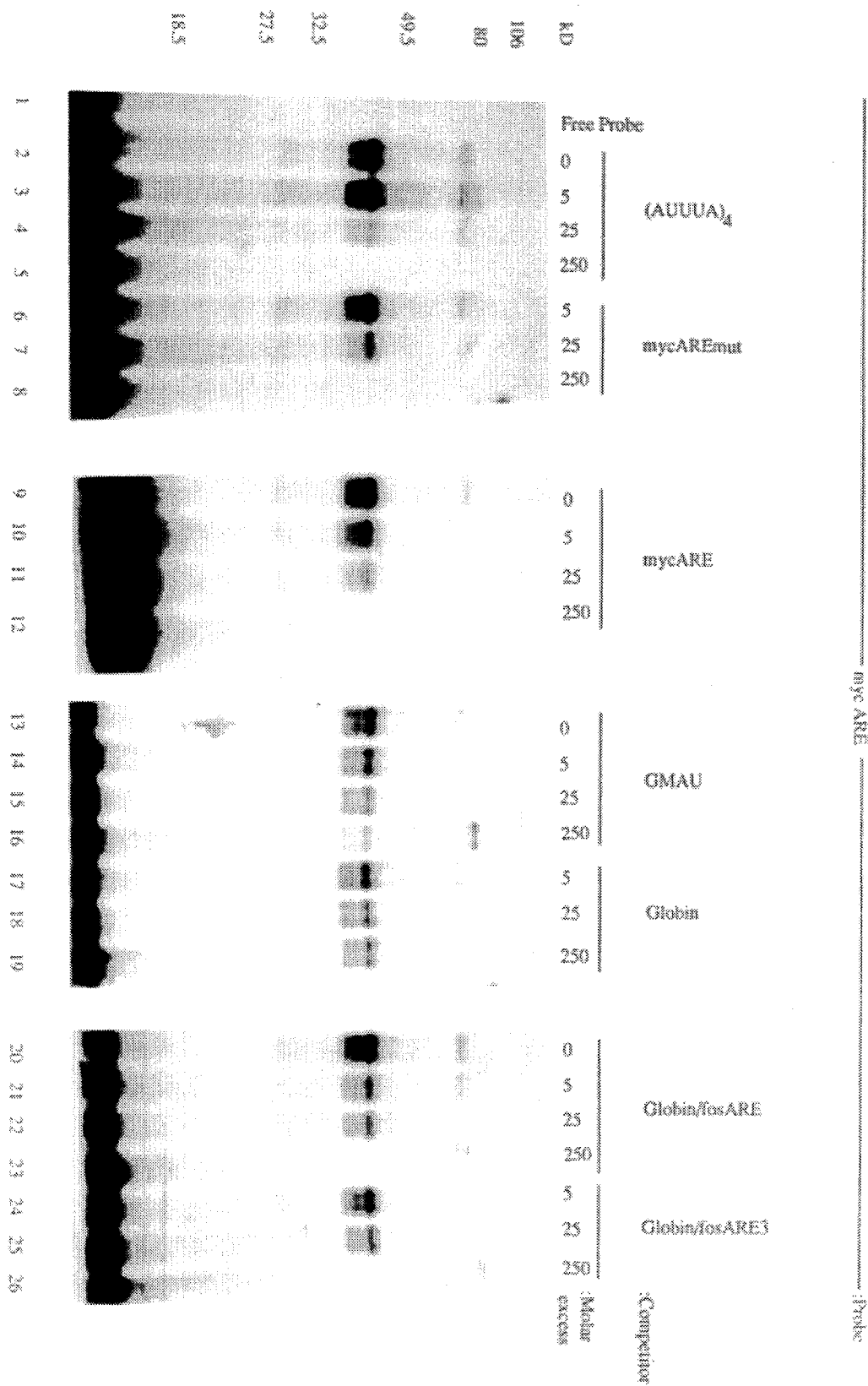
FIG. 2C represents an SDS-PAGE showing UV-crosslinking analysis of AUF1 to $^{32}$P-labeled c-myc ARE in the presence of excess unlabeled competitor RNAs.
Figure 2D:
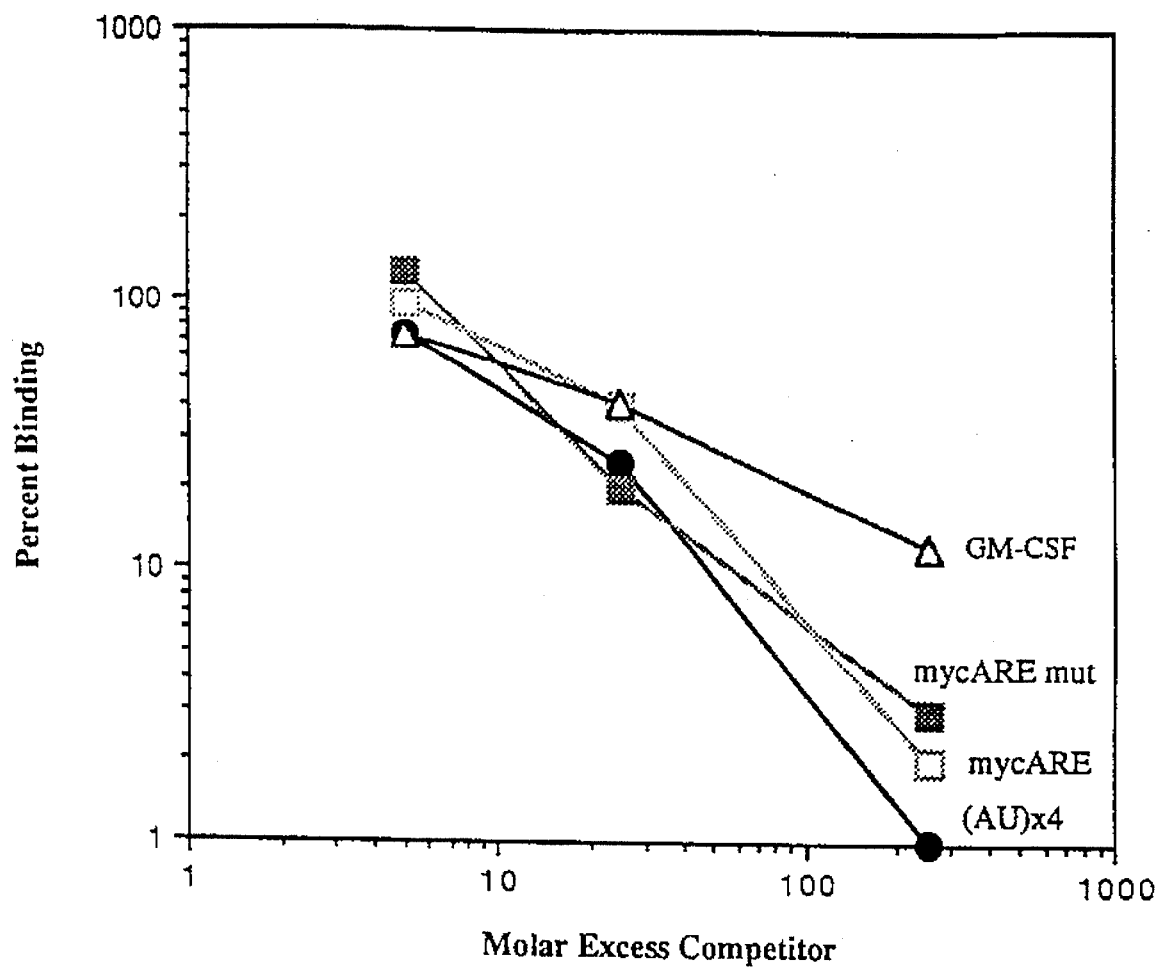
FIGS. 2D and 2E are graphs showing the AUF1 to RNA percent binding (compared to no competitor) plotted versus the molar excess of competitor indicated to the right of each curve; the plots were obtained by soft laser densitometry scan of the SDS-PAGE autoradiographs of FIG. 2C.
Figure 2E:
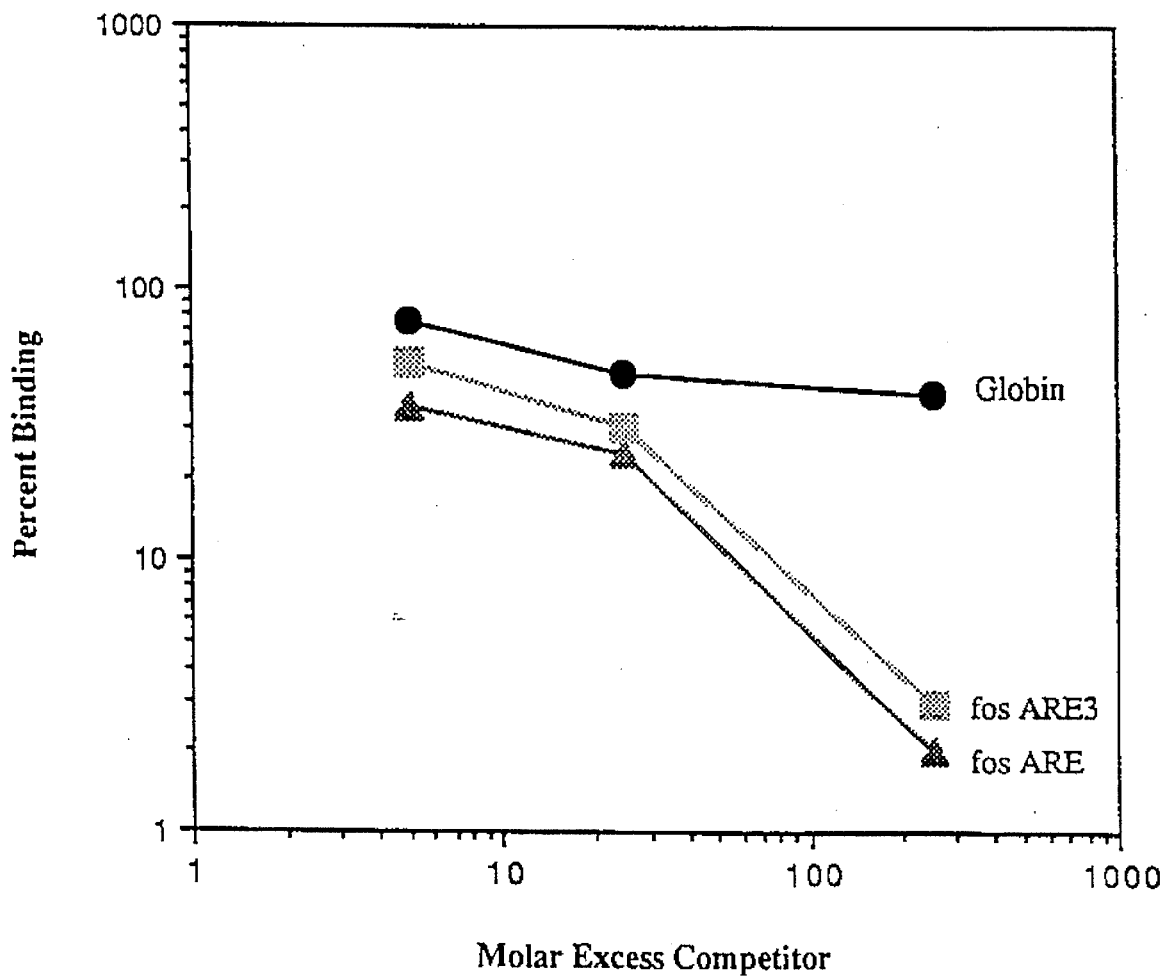

To confirm the specificity of binding by AUF1, various unlabeled competitor RNAs were added to the UV-crosslinking assays. A 250-fold molar excess of ARE RNAs (wild-type and mutant) reduced binding by AUF1 to 1%–12% of maximum binding (FIG. 2C, lanes 2–16 and 20–26; FIG. 2D and 2E) while β-globin reduced binding by only 50% (FIG. 2C, lanes 17–19; FIG. 2D and 2E). Collectively, the UV-crosslinking experiments indicate that, (1) AUF1 binds to RNA containing four tandem repeats of AUUU and to ARE of c-myc, c-fos and GM-CSF, and (2) in the context of the c-myc or c-fos ARE, intact AUUUA pentanucleotides are not required for binding. The correlation between AUF1 binding in vitro (FIG. 2) and rapid deadenylation of the mRNAs in cells (Schiavi et al., *Biochim. Biophy. Acta* 1114:95–106 (1992)) show that AUF1 is involved in the first step of ARE-mediated mRNA degradation in cells.

Immunological Characterization of AUF1

Figure 3A:
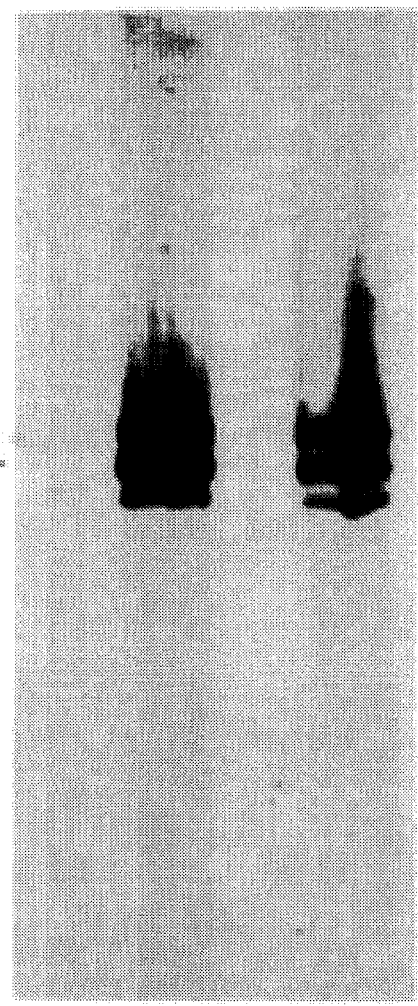
Figure 3B:
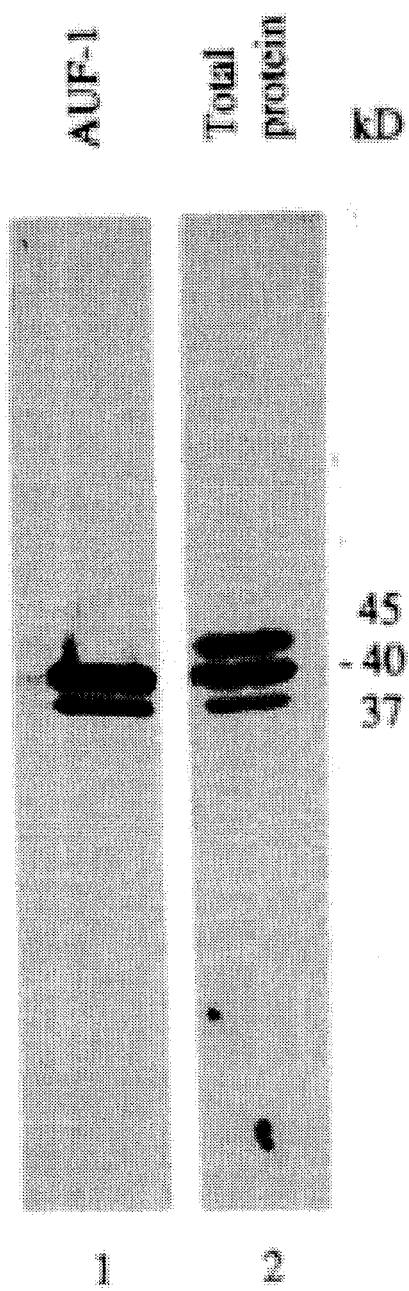

The poly(U)-agarose eluate (FIG. 1A, fractions 15–20) was used to immunize a rabbit for production of polyclonal antiserum. Affinity-purified, monospecific antibodies to the 40 kD polypeptide (p40) were prepared as described in Example 5. Pre-immune serum was mock affinity-purified by a procedure identical to that for preparation of α-p40. Sera were tested in a Western blot assay with nitrocellulose strips containing electrophoretically-separated total cell protein from K562 cells. Neither pre-immune nor mock affinity-purified, pre-immune sera reacted with any polypeptides (FIG. 3A, lanes 1 and 3). Both whole immune serum and affinity-purified α-p40 antibody detected three polypeptides of 37, 40 and 45 kD (FIG. 3A, lanes 2 and 4, respectively). This result shows that the three polypeptides are immunologically related. Because the 45 kD band (p45) was unexpected, Western blots of total cell protein and purified AUF1 were compared using α-p40. No p45 was detected in purified AUF1 preparations under conditions in which it was readily detected in total protein (FIG. 3B, lanes 1 and 2). To confirm that p45 was immunologically related to p37/40, α-p40 antibody was preincubated with various amounts of AUF1 (p37/40) protein, then reacted with nitrocellulose strips of total protein. Incubation with purified AUF1 resulted in a loss of reactivity of α-p40 with p45 and p40; p37 was too faint to observe (FIG. 3C, lanes 1–5). Again, this shows that p45 is immunologically related to p37/p40.

Figure 3D:
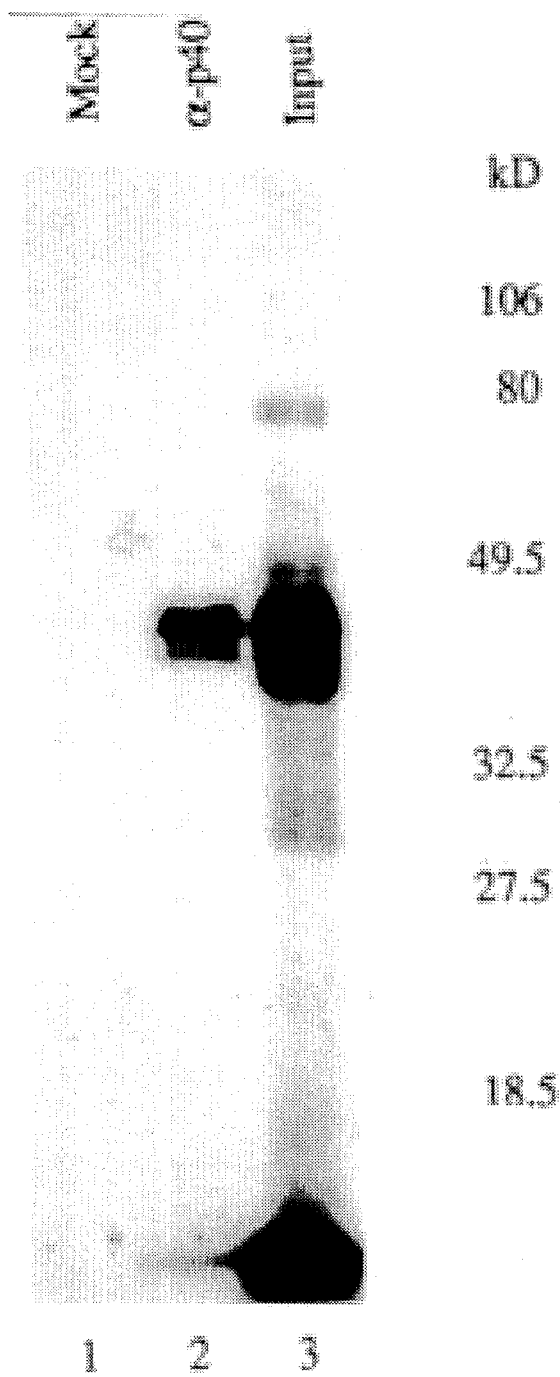
FIG. 3D represents a SDS-PAGE showing UV-crosslinking of AUF1 to $^{32}$P-labeled c-myc ARE and immunoprecipitation analysis.

To prove that the α-p40 antibody reacted with an ARE-binding protein, UV-crosslinking experiments were combined with immunoprecipitation. AUF1 protein was mixed with $^{32}$P-labeled c-myc ARE, irradiated with UV light and treated with RNase A as described for FIG. 2. Reactions were immunoprecipitated with either α-p40 or mock affinity-purified preimmune antiserum. Polypeptides were visualized by SDS-PAGE and autoradiography. Polypeptides of 37 and 40 kD were observed following immunoprecipitation with α-p40 but not with mock treated preimmune antiserum (FIG. 3D, lanes 1 and 2). The above shows that the α-p40 antibody recognizes the 37 and 40 kD RNA-binding species of AUF1.

Figure 4A:
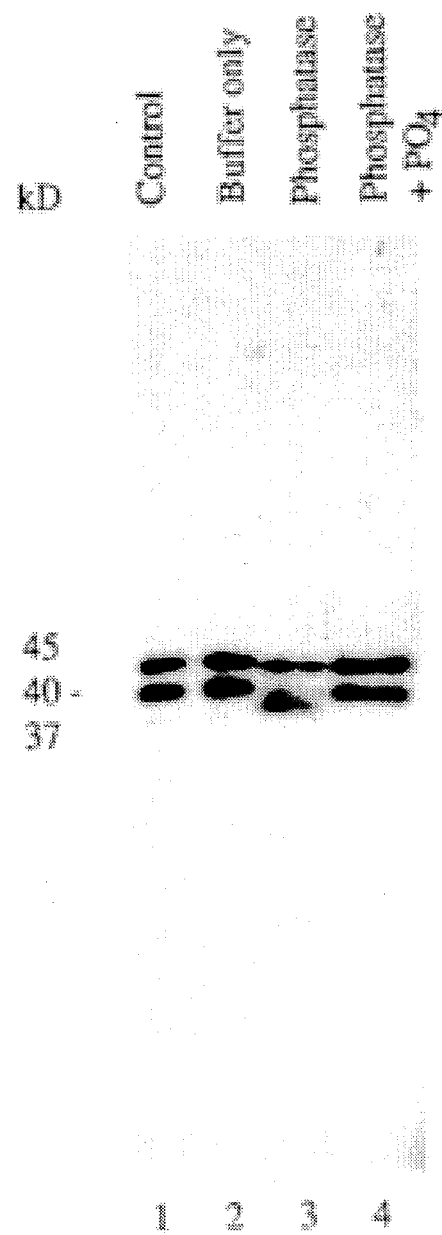
FIGS. 4A and 4B represent Western blot analyses of phosphorylated AUF1.
Figure 4B:
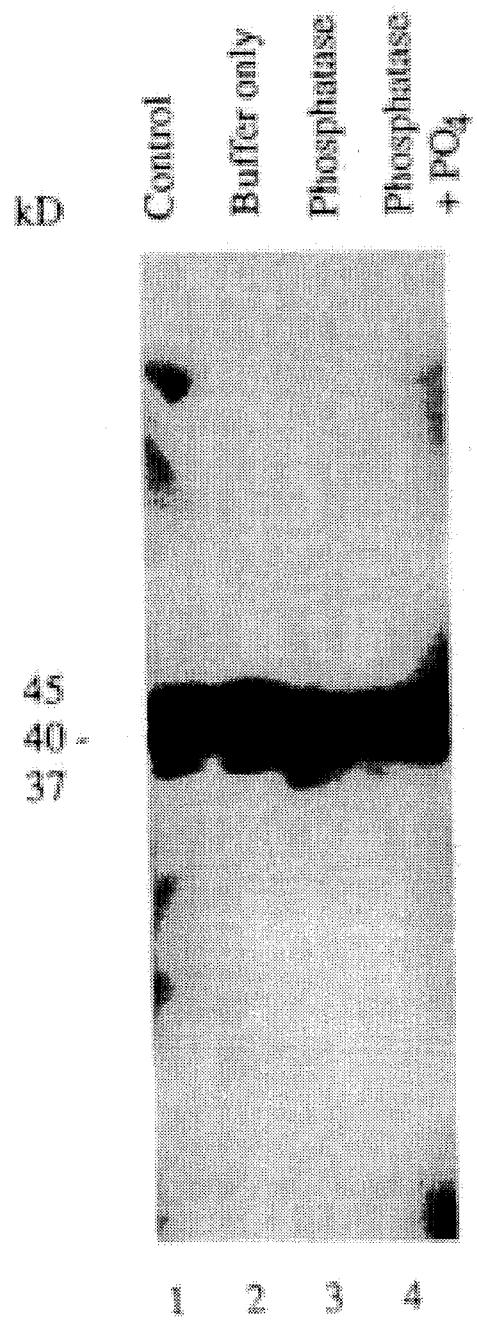
Figure 4C:
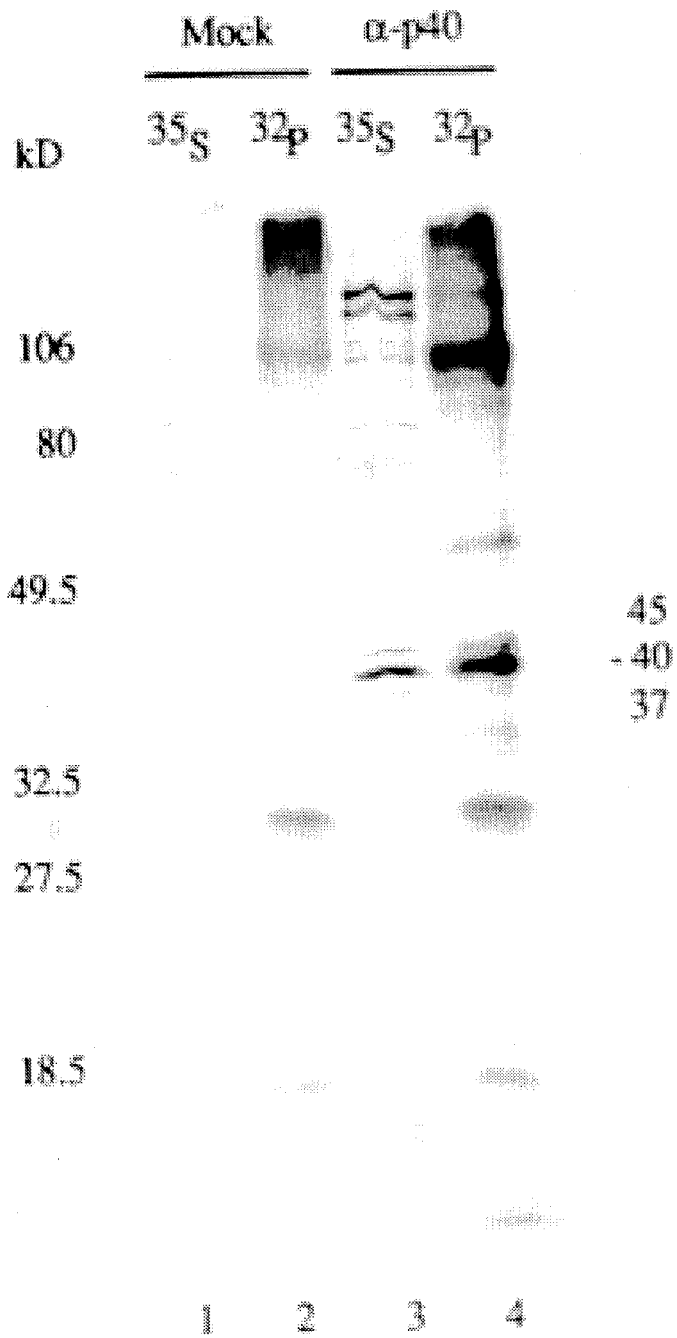
FIG. 4C represents a SDS-PAGE showing metabolic labeling and immunoprecipitation of AUF1.

To determine if these polypeptides are phosphorylated, whole cell protein was treated with potato acid phosphatase and analyzed by Western blotting with α-p40. p40 appears to increase in electrophoretic mobility, while p45 does not (FIG. 4A, lane 3). The presence of phosphate during the incubation prevented the mobility shifts, shows that the shifts are due to loss of phosphate groups (FIG. 4A, lane 4). A 4-fold longer autoradiographic exposure permitted detection of the 37 kD species in the control lane (FIG. 4B, lane 1). These results show that one or more species are phosphorylated. Confirmation of phosphorylation was obtained by metabolic labeling of K562 cellular proteins with either $^{35}$S-methionine or $^{32}$P-labeled phosphoric acid followed by immunoprecipitation analysis with α-p40 antibody. The $^{35}$S lysate clearly shows the 40 kD species and, to a lesser extent, the 37 and 45 kD species; the $^{32}$P lysate shows the 40 and 45 kD species and, to a lesser extent, the 37 kD species (FIG. 4C, compare lane 3 with lane 4). Immunoprecipitation control lanes showed no polypeptides in this size range (FIG. 4C, lanes 1 and 2). Together, these results indicate that each polypeptide is phosphorylated. Treatment of purified AUF1 with potato acid phosphatase did not ablate its RNA-binding activity.

Subcellular Localization of p37, p40 and p45

Figure 5:
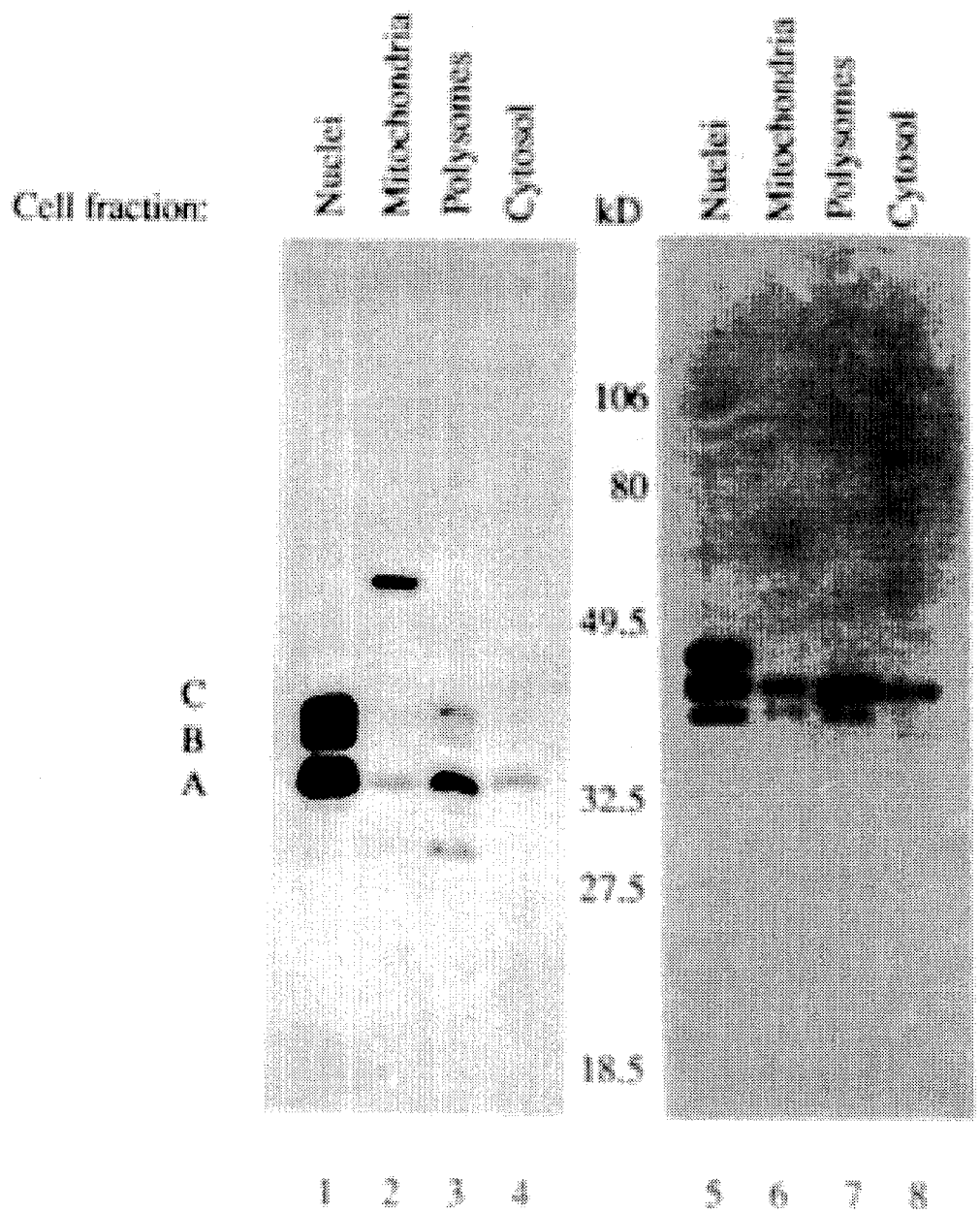
FIG. 5 represents a Western blot analysis showing the subcellular localization of the AUF1 polypeptide.

Antibodies to p40 reacted with p37, p40 and p45 in total cellular protein, yet p45 was not detected in purified AUF1 (FIG. 3). Therefore, the subcellular location of each polypeptide was examined by Western blot analysis of $10^6$ cell equivalents of nuclear, mitochondrial, polysomal and cytosolic (S130) fractions of K562 cells using α-p40. p37 and p40 were present in the nucleus (FIG. 5, lane 5) and cytoplasm, notably in the polysome fraction (FIG. 5, lanes 6–8). However, p45 was located exclusively in the nuclear fraction (FIG. 5, lane 5). This might explain why p45 was not detected in AUF1, since AUF1 was purified using S130 as the starting material. As a control for the subcellular fractionation, fractions were analyzed by Western blot assay using monoclonal antibody 4E4 which reacts with the human hnRNP A1/A2, B1/B2 and C1/C2 polypeptides (Wilusz and Shenk, *Mol. Cell. Biol.* 10:6397–6407 (1990)). These polypeptides were predominantly nuclear (FIG. 5, lanes 1–4) as reported (Pinol-Roma and Dreyfuss, *Science* 253:312–314 (1991); Pinol-Roma and Dreyfuss, *Nature* 355:730–732 (1992)). The presence of these hnRNP proteins in various cytoplasmic fractions (albeit at lower amounts compared to the nuclear fraction) is consistent with their presence in the cytoplasm due to shuttling between the nucleus and cytoplasm (Pinol-Roma and Dreyfuss, Ibid.). These results suggest that p37 and p40 did not leak from the nucleus during fractionation procedures. Further confirmation of this is suggested by the restricted localization of p45 to the nucleus.

Isolation and Characterization of an AUF1 cDNA Clone

Figure 6A:
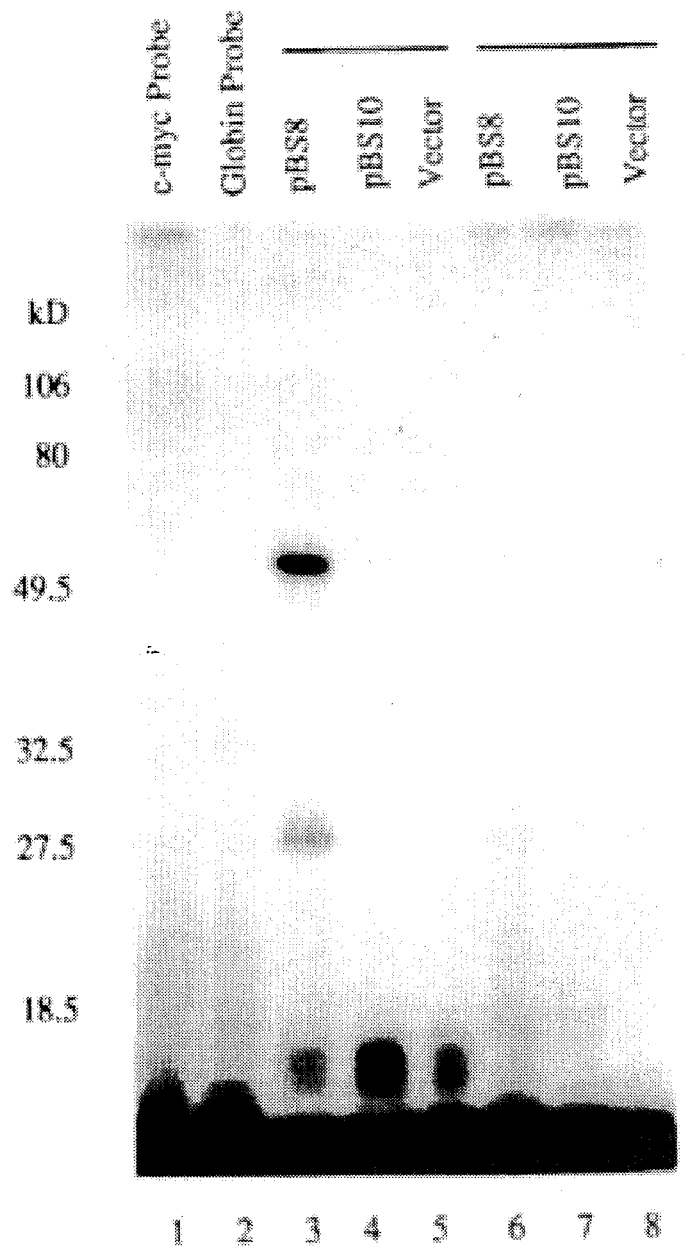
FIG. 6A represents a SDS-PAGE showing a UV-crosslinking analysis of fusion protein pBS8 to $^{32}$P-labeled c-myc ARE.
Figure 6B:
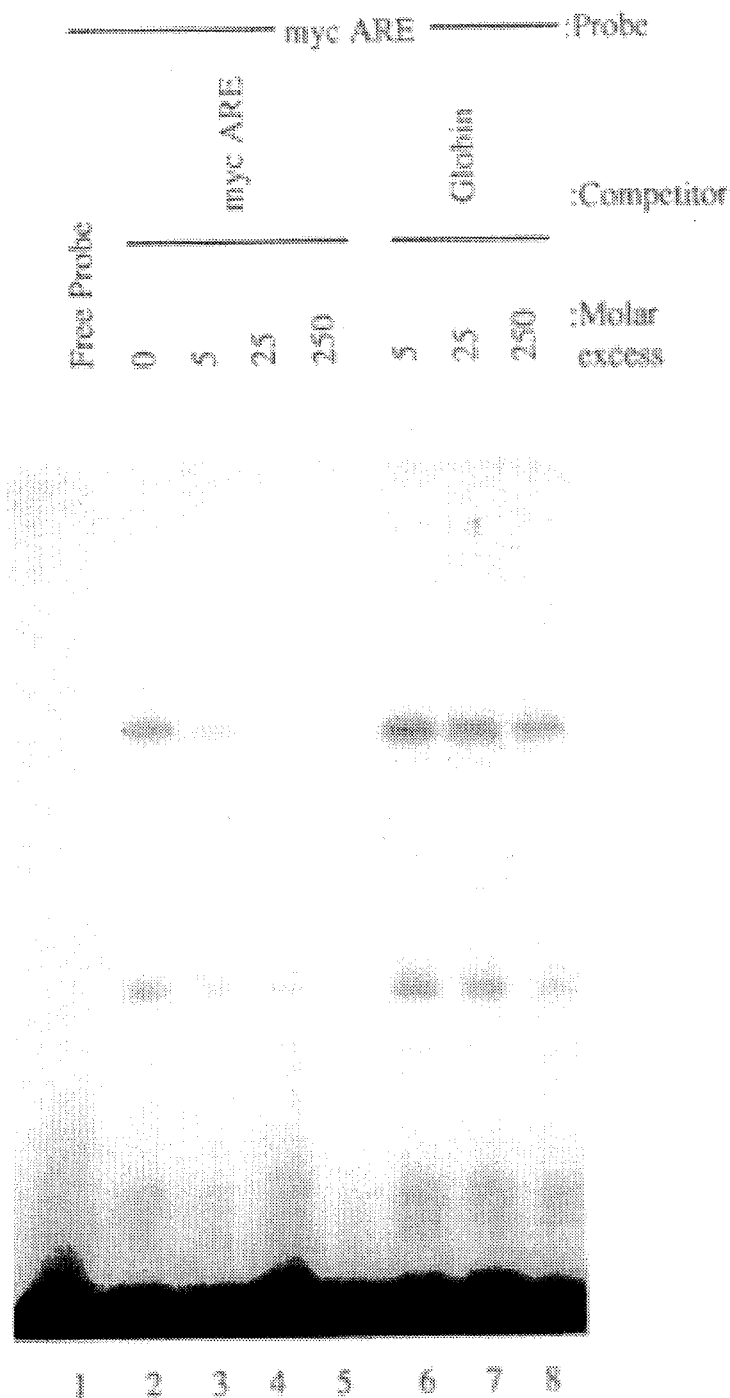
FIG. 6B represents a SDS-PAGE showing a UV-crosslinking analysis of fusion protein pBS8 to $^{32}$P-labeled c-myc ARE in the presence of excess unlabeled competitor RNAs.
Figure 6C:
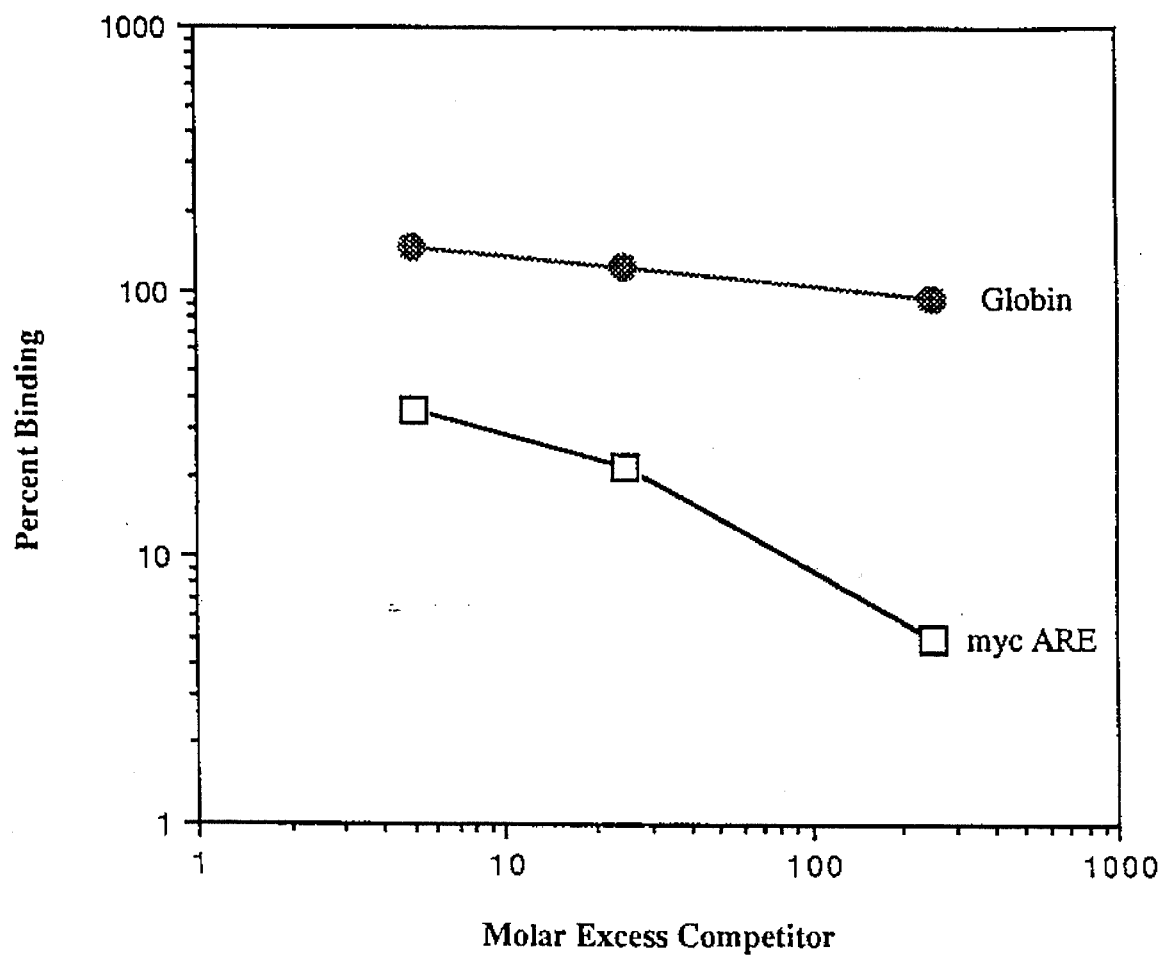
FIG. 6C is a graph showing the AUF1 to RNA percent binding (compared to no competitor) plotted versus the molar excess of competitor indicated to the right of each curve; the plots were obtained by soft laser densitometry scan of the SDS-PAGE autoradiographs of FIG. 6B.

Western blot analysis indicated that AUF1 is present in HeLa cells. Screening of 600,000 clones from a HeLa λ ZAP II expression library with affinity-purified α-p40 antibody resulted in the isolation of positive clones designated pBS8 and pBS10 encoding fusion proteins that reacted with the specific antibody. To test ARE-binding activity of the recombinant proteins, bacterial lysates of pBS8, pBS10 or vector alone were used in a UV-crosslinking assay with riP-labeled c-myc ARE or riP-labeled β-globin 3'UTR. The 55 kD fusion protein (derived by fusion of the β-galactosidase open reading frame with the AUF1 5'UTR and AUF1 open reading frame) encoded by pBS8 specifically crosslinked to the c-myc ARE but not β-globin 3'UTR (FIG. 6A, compare lane 3 with lane 6). Protein from the pBS10 and vector-only lysates did not support crosslinking to either the c-myc ARE or β-globin 3'UTR (FIG. 6A, lanes 4 and 7 and lanes 5 and 8, respectively). Thus the pBS10 protein contains an epitope allowing cross-reactivity to the α-p40 antibody, but the protein lacks RNA-binding activity. To substantiate the RNA-binding specificity of the BS8 fusion protein, UV-crosslinking experiments were performed with protein from BS8, $^{32}$P-labeled c-myc ARE and either unlabeled c-myc ARE or β-globin 3'UTR as competitors. Unlabeled c-myc ARE lowered binding to 5% at 250-fold molar excess while unlabeled β-globin 3'UTR had little, if any, effect on binding even at 250-fold molar excess (FIGS. 6B and 6C). These data suggested that the BS8 fusion protein binds to the c-myc ARE but not to β-globin 3'UTR. Direct evidence that pBS8 encodes an ARE-binding protein was obtained by immunoprecipitation of the protein crosslinked to the c-myc ARE using α-p40 antibody. The BS8 bacterial lysate was mixed with $^{32}$P-labeled c-myc ARE, irradiated with UV light and treated with RNase A. The mixture was immunoprecipitated with α-p40 or mock-purified preimmune antibody. Protein was visualized by SDS-PAGE and autoradiography. Reactions with α-p40 precipitated the 55 kD fusion protein 4-fold more efficiently than the control reactions (FIG. 6D), indicating that the BS8 fusion protein is an ARE-binding protein recognized by the α-p40/AUF1 antibody.

Figure 7:
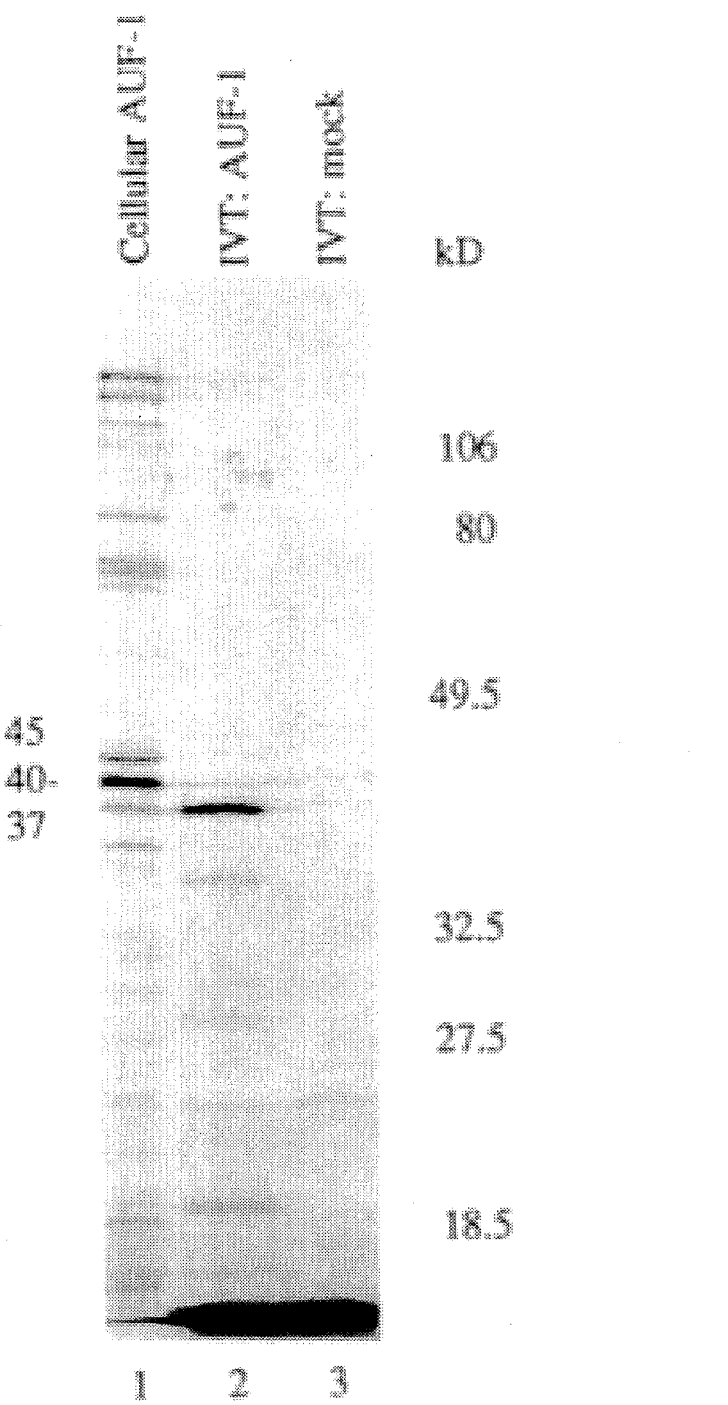
FIG. 7 represents a SDS-PAGE showing the in vitro translation product from AUF1 cDNA clone pBS8.

To determine which polypeptide species of AUF1 is encoded by the pBS8 cDNA, an in vitro translation experiment was performed. pBS8 cDNA was used as a template for RNA synthesis by T7 RNA polymerase. This RNA was used to program protein synthesis in a reticulocyte lysate in the presence of $^{35}$S-methionine. Translation produced a major 37 kD species (FIG. 7, lane 2) which co-migrates with p37AUF1 in immunoprecipitates of lysates from K562 cells metabolically labeled with $^{35}$S-methionine (FIG. 7, lane 1). As a control, translation without added RNA resulted in no detectable polypeptide products in this size range (FIG. 7, lane 3). Together these data strongly suggest that the pBS8 cDNA corresponds to the 37 kD species of AUF1. Therefore, this cDNA is hereafter referred to as p37$^{AUF1}$.

Figure 8D:
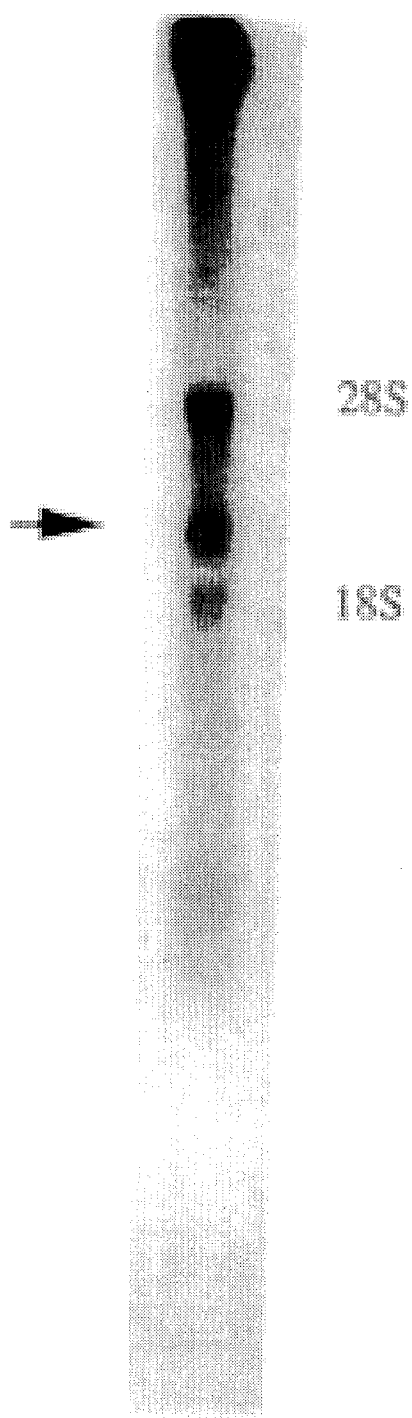
FIG. 8D shows the Northern blot analysis of AUF1 mRNA.

Sequence Analysis of p37$^{AUF1}$ p37$^{AUF1}$ (pBS8) was sequenced completely on both strands (FIGS. 8A, 8B, and 8C SEQ ID NO:4). The cDNA is 2,562 bp in length. A single open reading frame was consistent with the production of a β-gal fusion protein in the phage isolate. The first ATG at position 246 is in a good context for initiation of translation, with an A$^{-1}$ (Kozak, *J. Biol. Chem.* 266:19867–19870 (1991)). Assuming this is the authentic initiation codon, the ORF extends to position 1106 and encodes a polypeptide with a predicted $M_r$ of 32,000 daltons. The 5'UTR is at least 245 nt in length. The cDNA should not be significantly larger than 2.5 kb, since Northern blot analysis of poly(A+) RNA from K562 cells reveals a band of approximately 2.5 kb in addition to some cross-hybridization with contaminating 28S and 18S ribosomal RNAs (FIG. 8D). The 3'UTR is unusually long (at least 1.4 kb) and contains one ATTAAA polyadenylation signal (Proudfoot, *Cell* 64:671–674 (1991)) at position 1799. There is most likely an additional polyadenylation signal not present in the cDNA, since Northern analysis indicates that p37$^{AUF1}$ mRNA is approximately 2.5 kb in length. Typically, a proximal polyadenylation site is used at 5%–20% the efficiency of a distal site (Laird-Offringa et al., *Nuc. Acids Res.* 17:6499–6514 (1989) and references therein). The 3'UTR of p37$^{AUF1}$ cDNA contains three ATTTA and two ATTTTA motifs.

The MOTIFS subroutine of the Genetics Computer Group software (Devereux, et al., *Nuc. Acids Res.* 12:387–396 (1984)) was used to analyze the p37$^{AUF1}$ cDNA sequence. p37$^{AUF1}$ contains phosphorylation sites for cAMP-dependent protein kinase, protein kinase C, casein kinase II and tyrosine phosphokinase (Kemp and Pearson, *Trends Biochem. Sci.* 15:342–346 (1990)). p37$^{AUF1}$ contains two RNP consensus-type RNA-binding motifs also referred to as RNA recognition motifs or RRM (Bandzuilis et al., *Genes Dev.* 3:431–437 (1989); Frankel et al., *Cell* 67:1041–1046 (1991); Mattaj, *Cell* 57:1–3 (1989); Zamore et al., *Nature* 348:485–486 (1990)). An RRM is a 90-amino-acid domain containing a conserved 8-amino-acid consensus sequence (R/K)GF(G/A)FVX(F/Y) SEQ ID NO:6, referred to as RNP-1, and a less conserved 6-amino-acid motif, referred to as RNP-2. Structural studies indicate that an RRM consists of a four-stranded anti-parallel β sheet with two α helices packed against one face of the sheet (Zamore et al., *Nature* 348:485–486 (1990)). RNP-1 and RNP-2 lie on the central two strands at the center of the β sheet. RRMs are found in three types of RNA-binding proteins: heterogenous nuclear ribonucleoproteins, splicing regulators and development-specific factors (Kim and Baker *Mol. Cell. Biol.* 13:174–183 (1993)). The C-terminal end of p37$^{AUF1}$ contains a glutamine-rich motif (KEQYQQQQQWGSRGG) SEQ ID NO:7. These motifs are thought to serve as protein-protein interaction sites in some RNA- and DNA-binding proteins (Bandzuilis et al., *Genes Dev.* 3:431–437 (1989); Courey and Tijan, *Cell* 55:887–898 (1988)).

Deposit of Strain Useful in Practicing the Invention

A deposit of biologically pure cultures of the following strain was made with the American Type Culture Collection, 12301 Parklawn Drive, Rockville, Md., the Collection, 12301 Parklawn Drive, Rockville, Md., the accession number indicated was assigned after successful viability testing, and the requisite fees were paid. Access to said culture will be available during pendency of the patent application to one determined by the Commissioner to be entitled thereto under 37 C.F.R. Section 1.14 and 35 U.S.C. Section 122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

The AUF1 cDNA sequence, inserted into the plasmid pBS8 in the strain *E. coli* XL-1 Blue, has been given ATCC No. 69349 and deposit date, Jul. 9, 1993.

Anti-tumor activity of AUF1 is demonstrated by modifying its expression in a non-tumorigenic cell line and examining the effects on cell growth. This is done in four ways: (1) overexpression in stably transfected cells, (2) transfection of dominant negative mutants, (3) nude mouse studies, and (4) antisense oligonucleotides.

1. Overexpression in stably transfected cells

The AUF1 cDNA is cloned into a eukaryotic expression vector containing a strong promoter and a gene allowing resistance to hygromycin. This construct is transfected into NIH3T3 cells, a mouse fibroblast cell line routinely used to define tumor suppressor genes. Control cells are transfected with the vector only. Cells are grown in hygromycin to select those cells that harbor the transfected DNA. After 2–3 weeks, the cells stably transfected with AUF1 die while the control cells do not. The significance is that cells require both positive and negative influences on growth. Too much negative regulation by AUF1 results in shutdown of genes required for normal cellular growth. This demonstrates that AUF1 has anti-tumor properties.

2. Transfection of dominant negative mutants

Dominant negative mutants have a partial loss of function. When overexpressed, they compete with the wild-type protein to knockout the function of the wild-type protein. The resultant cells become tumorigenic. AUF1 has two functions: it binds an AU-rich RNA sequence (RNA-binding function) present in many proto-oncogene mRNAs, and it binds other proteins to effect mRNA degradation (effector function). These two functions are modular in the AUF1 protein. Thus, mutations are introduced into the AUF1 cDNA such that either the RNA-binding or effector function of AUF1 is ablated. These constructs are stably transfected into NIH3T3 cells. Control cells are stably transfected with vector only. Cells harboring the transfected DNA are selected in hygromycin. After 2–3 weeks, foci form in the cell culture monolayer derived from cells transfected with dominant negative mutants of AUF1; control cells show no foci. The foci are visible clusters of cells which are easily counted. The potency of the dominant negative mutant is measured by the number of foci per 100,000 cells transfected. Individual foci are picked and expanded in culture to test for growth in soft agar. Control and focus-derived cells are plated in soft agar. Control cells do not grow in this medium (0% cloning efficiency) while focus-derived, transformed cells do (cloning efficiency 10–30%). Cloning efficiency is the number of colonies×100 divided by the number of cells plated.

3. Nude mouse studies

As an in vivo test of tumorigenicity of the focus-derived cell lines obtained by transfection of dominant negative mutants of AUF1, cells are injected into nude mice. Specifically, $10^6$ focus-derived cells are injected into the left flank of a nude mouse; equal numbers of control cells are injected into the right flank. Mice are inspected for 120 days for tumor formation that occurs in the left flank. No tumors form in the control, right flanks, of mice or in mice injected with control cells only. Cells from excised tumors still grow in hygromycin and express the dominant negative forms of AUF1. Moreover, these cells show elevated levels of proto-oncogene expression, demonstrating a role for the mutant AUF1 protein in transformation in vivo.

4. Antisense oligonucleotides

Deoxyoligonucleotides complementary to the 5' non-coding region and translation initiation codon of the AUF1 mRNA are added to cultures of cells. The oligonucleotides enter the cells. This blocks translation of the AUF1 mRNA and prevents synthesis of the protein. This serves as an alternative to the use of dominant negative mutants to effectively knockout expression of AUF1. After two-three weeks of continuous exposure to the oligonucleotides, foci form in the monolayer culture of cells. Cells treated with a control oligo show no foci. Foci are characterized and used in nude mouse assays as described above for studies utilizing dominant negative mutants.

For producing monoclonal antibodies, purified AUF1 is injected into mice at 3-week intervals for a total of 3 injections. After confirming antibody production by a test bleed, the spleen is removed. Spleen cells are fused to a mouse tumor cell line to immortalize the antibody producing cells. These antibody producing cell lines are cultured, and the culture supernatants are tested for reactivity to AUF1 by ELISA. Following identification of positive cell lines, the cells are cloned by limiting dilution to insure that the antibody is derived from only one cell type (i.e., is monoclonal). Each monoclonal antibody (MAb) is tested to determine the epitope recognized on the AUF1 molecule. Each is also tested to determine the assays that will permit the antibody to recognize AUF1 (e.g., Western blot, immunoprecipitation, indirect immunofluorescence in situ). The cell lines and their culture supernatants represent an unlimited supply of a particular MAb.

Loss of AUF1 levels or activity in cells leads to elevated proto-oncogene expression (e.g., c-myc and c-myb) leading in turn to neoplastic transformation. One example of elevated c-myc and c-myb expression is acute myeloid leukemia (AML). Overexpression is not due to detectable rearrangements of these genes but rather to mutation in a factor (AUF1) which serves to limit their expression in normal cells. Thus, the AUF1 MAbs are used as diagnostics to screen lysates of mononuclear cells from peripheral blood or bone marrow of AML patients to assess the loss of AUF1. Screening of the lysates is performed by Western blotting and/or ELISA. The degree of loss correlates with the severity of the AML. This information is used by the physician to determine how aggressive the treatment regimen should be.

The anti-tumor behavior of AUF1 is mediated by its affinity for an RNA sequence, known as an AU-rich element or ARE, present in the mRNA encoding proto-oncogene products such as c-myc and c-myb. The ARE targets these mRNAs for rapid degradation in normal cells. This degradation process serves to limit expression of the encoded proteins. Since the AUF1 cDNA is cloned into a bacterial expression vector, large amounts of the recombinant polypeptide can be easily purified. The recombinant polypeptide displays the same RNA-binding specificity and affinity as the cellular AUF1 protein. The ARE-binding affinity (i.e., dissociation constant, $k_D$) is easily measured by standard techniques (e.g., filter-binding assay, UV-crosslinking). Since the anti-tumor properties of AUF1 are dependent upon its affinity for the ARE, screening of pharmacologicals that enhance this activity is performed. This is done by mixing recombinant AUF1, radiolabeled ARE-RNA, and the test-drug and filtering through a nitrocellulose membrane. The counts per minute (cpm) retained on the membrane is a function of the binding affinity of AUF1 for the ARE. This is a rapid, convenient and quantitative assay to screen drugs that increase the anti-tumor capability of AUF1. The most effective drugs in this in vitro test are used to treat leukemia cells in culture to assess the drug's ability to enhance the anti-tumor activity of endogenous AUF1 protein. This is measured by slowed growth rate and maturation of the leukemia cells to a population with limited proliferative capability (like normal cells).

Pharmacological are also tested to identify those that lower the affinity of AUF1 for the ARE in the assay described above. This results in elevated expression of genes involved in promoting growth. These drugs have utility in promoting proliferation of cells that have ceased to divide. This is particularly useful with cells of neural origin. For example, these drugs permit regeneration of cells damaged during spinal cord injury.

The recombinantly produced AUF1 polypeptide can be used in the treatment of individuals determined to have low levels of the AUF1 gene. To prevent the formation of tumors in these individuals, the AUF1 polypeptide is administered therapeutically to these individuals.

The following examples are presented to illustrate the present invention and to assist one of ordinary skill in making and using the same. The examples are not intended in any way to otherwise limit the scope of the invention.

EXAMPLE 1

Purification of AUF1

A 130,000×g post-ribosomal supernatant (S130) was prepared from human erythroleukemia K562 cells (Dean et al., *Proc. Natl. Acad. Sci. USA* 80:5515–5519 (1983); Lozzio and Lozzio, *Blood* 45:321–334 (1975)) by lysis in buffer A (10 mM Tris-HCl (pH 7.6), 1 mM magnesium acetate, 1.5 mM potassium acetate, 2 mM dithiothreitol (DTT), 1 µg/ml each of leupeptin and pepstatin A, 0.1 mM phenylmethylsulfonyl fluoride (PMSF) as described previously (Brewer and Ross, *Meth. Enzymol.* 181B:202–209 (1990)). Eight grams of S130 protein from sixty liters of K562 cells (approximately $2.5 \times 10^{10}$ cells total) were shaken for 5 hours at 4° C. with 300 ml of heparin-agarose beads (Sigma) which had been equilibrated with buffer A+0.1M potassium acetate. Heparin-agarose was washed with 2.5 column volumes of buffer A+0.25M potassium acetate. Bound proteins were eluted with 200 ml of buffer A+1M potassium acetate.

A 1 ml column of poly(U)-agarose (Type 6: Pharmacia) was equilibrated with 30 column volumes of buffer A+1M potassium acetate. The heparin-agarose eluate was adjusted to 50 µg/ml poly(C) and loaded onto the poly(U)-agarose column at a flow rate of 30 ml/hr at 4° C. The column was washed with 30 column volumes of buffer A+1M potassium acetate. Proteins were eluted from the poly(U)-agarose with a step gradient of increasing potassium acetate concentration (1M–4.5M in 0.5M increments with 3 ml/increment). ARE-binding activity of AUF1 was assayed as described (Brewer, *Mol. Cell. Biol.* 11:2460–2466 (1991)) by band-shift analysis using a $^{32}$P-labeled RNA containing a human c-myc ARE. Activity eluted primarily in fractions 15–20, corresponding to 3–3.5M potassium acetate. These fractions were pooled, dialyzed against buffer A+0.1M potassium acetate and concentrated to 200 µl using a Centricon 30 (Amicon). Typically, 270 µg of AUF1 were obtained from $2.5 \times 10^{10}$ cells. Amount of AUF1 was determined by SDS-PAGE and silver staining using various concentrations of BSA as standards.

In FIG. 1A, the polypeptide profile is represented by the silver-stained SDS-polyacrylamide gel of all fractions from the poly(U)-agarose column. One hundred microliters of each 1 ml fraction was precipitated with TCA and run in a 10% SDS-polyacrylamide gel. The apparent molecular weights (in kD) of marker proteins (in lane M) are shown on the left. The bar above fractions 15–20 represents the fractions pooled, dialyzed and concentrated for use in other examples as noted. In FIG. 1B is an analysis of ARE-binding activity. The $^{32}$P-labeled probe was synthesized by in vitro transcription of SspI-digested pMycSD3, using SP6 RNA polymerase (Brewer, *Mol. Cell. Biol.* 11:2460–2466 (1991)). The ARE-containing probe is 196 nt of c-myc RNA sequence from the 3'UTR (positions 5616–5812 (Battey et al., *Cell* 34:779–787 (1983)) containing the 140 nt c-myc ARE (Jones and Cole, *Mol. Cell. Biol.* 7:4513–4521 (1987)). RNA-binding mixtures contained the RNA substrate and 2 µl of each 1 ml fraction. Free probe and protein-probe complexes were separated on a native 6% polyacrylamide gel and exposed to film. The complexes were scanned by soft-laser densitometry and plotted as percent of maximum ARE-binding activity.

EXAMPLE 2

Construction of Plasmids and In Vitro Transcription

Plasmid pGEMmyc (AT1) was derived from plasmid pMycSD3 (Brewer, *Mol. Cell. Biol.* 11:2460–2466 (1991)) by introducing a SmaI site at the first polyadenylation site by PCR. The SacI-SmaI fragment, containing the ARE, was cloned into SacI-SmaI digested plasmid pGEM-7Zf(+) (Promega) such that transcription with SP6 RNA polymerase yields sense RNA. Plasmid pGEMmycARE(mut) was derived from pGEMmyc(AT1) by site directed mutagenesis. Specifically, the two ATTTA motifs (indicated by the underlines below) were disrupted by single T-to-A mutations (indicated by the bold letters below) resulting in the sequence 5'-CATCTTTTTTTTTTCTTTAACA-GATTTGT<u>ATATA</u>AGAATTGTTTTTAAAAAATTTTAAG <u>ATATA</u>CAC-3'SEQ ID NO:8. Plasmid pSP64GMΔAU(NcoRI) was derived from pSP64GMΔAU+ATG (Kruys et al., *Science* 245:852–855 (1989)) by digestion with NcoI and HindIII and ligation of the large fragment to produce a plasmid with the human GM-CSF 3'UTR, lacking the 83 nt ARE, in the sense orientation for SP6 transcription. Plasmids pα19Rβ, pα19Rβ+ARE and pα19Rβ+ARE3 were derived from plasmids pBBB, pBBB+ARE and pBBB+ARE3 (Shyu et al., *Genes Dev.* 5:221–231 (1991)), respectively, by cloning the EcoRI-KpnI fragment containing the rabbit β-globin 3' end (and c-fos ARE sequences) into the EcoRI-KpnI site of plasmid pT7/T3α19 (BRL). In vitro transcription reactions were performed with linearized templates and either SP6, T7 or T3 RNA polymerase (Brewer and Ross, *Mol. Cell. Biol.* 8:1697–1708 (1988)). ($\alpha$-$^{32}$P)UTP was included for synthesis of radiolabeled RNAs.

EXAMPLE 3

Metabolic Labeling and Immunoprecipitation of AUF1

For metabolic labeling with $^{35}$S-methionine, $8 \times 10^6$ K562 cells in log phase were harvested, washed and incubated in 0.8 ml methionine-free RPMI-1640 with Tran$^{35}$S-label (ICN) (final concentration 150 µCi/ml) for 3 hr. at 37° C. For metabolic labeling with $^{32}$P, cells were washed and labeled in phosphate-free medium containing $^{32}$P-phosphoric acid (ICN) (final concentration 250 µCi/ml) for 3 hr. at 37° C. The labeled cells were harvested and washed with PBS. The labeled cell pellets were lysed using NP-40 lysis buffer (150 mM NaCl, 50 mM Tris-HCl (pH 7.5), 1% NP-40) on ice for 30 min. The lysate was sheared through a 22.5 gauge syringe needle 10 times and spun at 10,000×g for 10 min. to remove debris.

$10^6$ cell equivalents of lysate was used for each immunoprecipitation. Lysates were precleared as follows. One hundred microliters of lysate was incubated with 5 µl rabbit preimmune serum on ice for 1 hr. Fifty microliters of protein A cell suspension (Sigma) was washed with 0.5 ml PBS, incubated in 0.5 ml Blotto (5% non-fat dry milk) for 30 min., washed twice with 0.5 ml PBS and then once with 0.5 ml NET-gel buffer (50 mM Tris-HCl (pH 7.5), 150 mM NaCl, 0.1% NP-40, 1 mM EDTA, 0.25% gelatin, 0.02% sodium azide). The lysate-preimmune serum mixture was added to the blocked protein A cell pellets, mixed and incubated on a turning wheel for 30 min. at 4° C. and centrifuged at 12,000×g for 5 min.; the supernatant was used for immunoprecipitation as follows. Either mock affinity-purified preimmune serum or affinity-purified α-p40 antibody were added to the lysates. NET-gel buffer was added to a final volume of 0.5 ml. and incubated on ice for 1 hr. This was followed by incubation with protein A cells for another hour. The complexes were washed with RIPA buffer (Sambrook et al, Molecular Cloning: *A Laboratory Manual,* 2nd edition, Cold Spring Harbor Laboratory Press (1989)) three times and with 10 mM Tris-HCl (pH 7.5), 0.1% NP-40 one time. The protein A pellet was suspended in 30 µl SDS-PAGE loading buffer, boiled for 5 min, spun, and the supernatant was fractionated by 10% SDS-PAGE. Proteins were visualized by autoradiography.

EXAMPLE 4

Analysis of RNA-Binding by AUF1

Partial sequences of RNA-binding substrates containing ARE are used in UV-crosslinking to AUF1. The ARE from human c-myc, c-fos and GM-CSF are shown in FIG. 2A SEQ ID NO:1, SEQ ID NO:2, and SEQ ID NO:3. For c-myc and c-fos, the bold and underlined nucleotides were changed to A residues by site directed mutagenesis for the mutant RNA substrates. These mutant sequences are "myc AREmut" and "globin/fos ARE3", respectively. (Plasmids for wild type and mutant c-fos were provided by Dr. Ann-Bin Shyu., U. of Texas Health Science Center, Houston, Tex). For GM-CSF, the bold and underlined nucleotides were deleted in the mutant substrate "GMΔAU". (Plasmids for wild type and mutant GM-CSF were provided by Dr. Gray Shaw, Genetics institute, Cambridge, Mass.) The UV-crosslinking of AUF1 to RNA substrates is shown by the SDS-PAGE of FIG. 2B. AUF1 protein from the poly(U)-agarose column was silver stained (lane 2) or UV-crosslinked to equal cpm of the $^{32}$P-labeled RNA substrates indicated above each pair of lanes (lanes 3–20). Mixtures contained purified AUF-1 protein and 200,000 cpm of probe in a final volume of 10 µl 10 mM Tris-HCl (pH 7.5), 2 mM DTT, 100 mM KOAc, 5 mM Mg(OAc)$_2$, 0.1 mM spermine and 1 µg/µl poly(C). These mixtures contained either 1× or 3× amounts of protein to insure probe excess. Reaction mixtures were incubated on ice for 10 min. Then the reaction mixtures were irradiated with 254 nm UV light (energy of 0.25 J) for 3 min. at a distance of 15 cm in a Stratalinker apparatus (Stratagene). Next the mixtures were treated with 10 µg of RNase A (Sigma) at 37° C. for 30 min to digest free RNA. Protein crosslinked to $^{32}$P-labeled RNA was separated by 10% SDS-polyacrylamide gel electrophoresis under reducing conditions and visualized by autoradiography. Plasmid templates were as follows. Plasmid pα19d2 (Malter, *Science* 246:664–666. (1989)) digested with EcoRI and transcribed with T7 RNA polymerase produces 76 nt "(AUUUA)$_4$" RNA containing the sequence AUUUAUUUAUUUAUUUA SEQ ID NO:9. Plasmid pT7/T3α19 digested with EcoRI and transcribed with T7 RNA polymerase produces 59 nt "nonspec." RNA. Plasmid pGEMmyc(AT1) digested with SspI and transcribed with SP6 RNA polymerase produces 227 nt "myc ARE" RNA. Plasmid pGEMmycARE(mut) digested with SspI and transcribed with SP6 RNA polymerase produces 227 nt "myc ARE mut" mutant c-myc RNA. Plasmid pSP64GM(NcoRI) digested with EcoRI and transcribed with SP6 RNA polymerase produces a 230 nt "GMAU wild-type GM-CSF": RNA (Brewer, *Mol. Cell. Biol.* 11:2460–2466 (1991)). Plasmid pSP64GMΔAU(NcoRI) digested with EcoRI and transcribed with SP6 RNA polymerase produces 147 nt "GMΔAU" mutant GM-CSF RNA.

Plasmid pα19Rβ digested with BglII and transcribed with T3 RNA polymerase produces 70 nt "globin" 3'UTR RNA. Plasmid pα19Rβ+ARE digested with BglII and transcribed with T3 RNA polymerase produces 145 nt "globin/fos ARE" RNA. Plasmid pα19Rβ+ARE3 digested with BglII and transcribed with T3 RNA polymerase produces 145 nt "globin/fos ARE3" mutant c-fos RNA. The results of competition experiments with $^{32}$P-labeled c-myc ARE are shown in the SDS-PAGE of FIG. 2C. For competition experiments, AUF-1 and $^{32}$P-labeled probe c-myc ARE substrate were mixed simultaneously with 5-, 25- or 250-fold molar excess of unlabeled RNAs as indicated above each Figure. Following incubation, mixtures were irradiated and treated with RNase A as described above. Proteins were visualized by SDS-PAGE and autoradiography. The numbers above each Figure indicate the molar excess of competitor. Molecular weights are indicated at the left of the FIG. FIGS. 2D and 2E are graphs showing the quantitation of RNA-binding activity. The autoradiographs in FIG. 2C were scanned by soft laser densitometry. In FIGS. 2D and 2E, the percent binding (compared to no competitor) is plotted versus the molar excess of competitor indicated to the right of each curve.

EXAMPLE 5

Characterization of an Anti-AUF1 Polyclonal Antibody

Anti-AUF1 antibodies were prepared using the poly(U)-agarose fractions 15–20 (Example 1) as immunogen. Approximately 50 µg of eluate was injected at each of three 2-week intervals (150 µg total) into a New Zealand White rabbit. For affinity purification of antibody to p40, a preparative SDS/polyacrylamide gel was run with AUF1 protein (poly(U)-agarose eluate) and transferred to a nitrocellulose sheet. The sheet was stained with India ink to localize p40, which was cut from the membrane with a scalpel. The strip was cut into small pieces and incubated with 1 ml of whole immune serum at room temperature for 2 hours. The strip was washed extensively with PBS; antibody was eluted with 1 ml of 100 mM glycine, pH 2 and immediately neutralized with 0.1 ml of 1M Tris. For control experiments, preimmune serum was subjected to the same affinity purification procedure as the immune serum. Both affinity-purified α-p40 antibody and mock-purified preimmune serum were used at a 1:50 dilution in Western blot assays; whole sera were used at a 1:10,000 dilution. The Western blot analysis of FIG. 3A represents the test of whole sera and affinity-purified antibodies. Nitrocellulose strips of K562 total cell protein were incubated with either whole sera (preimmune in lane 1 and immune in lane 2) or affinity-purified antibody (mock in lane 3 and α-p40 in lane 4). The blot was developed with $^{125}$I-protein A. In FIG. 3B, the Western blot analysis shows a comparison of AUF1 and total K562 cell protein. Separate strips of AUF1 (lane 1) and total cell protein (lane 2) were tested with α-p40 antibody by Western blot. The immunoabsorption of α-p40 antibody with purified AUF1 protein is shown by the Western blot analysis of FIG. 3C. Affinity-purified α-p40 antibody was incubated with the indicated amounts of purified AUF1 (lanes 1–5) in a final volume of 60 µl overnight at 4° C. The antibody was then diluted 50-fold to test each nitrocellulose strip of total cell protein by Western blot. The locations of 45-, 40- and 37 kD polypeptides are indicated in each FIG. The results of UV-crosslinking and immunoprecipitation analysis is shown in the SDS-PAGE of FIG. 3D. AUF1 was crosslinked to $^{32}$P-labeled c-myc ARE and treated with RNase A as described in FIGS. 2B and 2C. Reactions were either not precipitated (lane 3) or immunoprecipitated with mock purified preimmune (lane 1) or α-p40 antibody (lane 2). Polypeptides were visualized by SDS-PAGE and autoradiography.

EXAMPLE 6

Phosphorylation of AUF1

In FIG. 4A is a Western blot analysis representing phosphatase treatment of K562 cellular protein. Approximately 20 μg of total cell protein was treated with 0.7 U of potato acid phosphatase or mock treated at 37° C. for 1 hour. Reactions were analyzed by Western blotting with affinity-purified α-p40 antibody. Molecular weights in kD are indicated at the left of the panel. Lanes: 1, control, no treatment; 2, addition of phosphatase buffer without enzyme and incubated 1 hour; 3, phosphatase added and incubated 1 hour; 4, same as lane 3 but 50 mM sodium phosphate included during phosphatase incubation as a control. FIG. 4B is a 4-fold longer exposure of FIG. 4A. This exposure shows p37 which is faint in FIG. 4A. The metabolic labeling and immunoprecipitation of AUF1 is shown by the SDS-PAGE of FIG. 4C. Lysates were prepared from K562 cells metabolically labeled with either $^{35}$S-methionine (lanes 1 and 3) or $^{32}$P (lanes 2 and 4) and immunoprecipitated with either mock, affinity-purified preimmune serum (lanes 1 and 2) or α-p40 (lanes 3 and 4). Immune complexes were subjected to SDS-PAGE and polypeptides were visualized by autoradiography.

EXAMPLE 7

Subcellular Localization of AUF1 Polypeptide

The subcellular localization of AUF1 polypeptide is shown in FIG. 5 by Western Blot analysis. A one liter culture of K562 cells (6×108 cells total) was harvested and washed in RPMI-1640 without serum. All subsequent procedures were performed at 4° C. Cells were lysed in 7.5 ml of buffer A (described in Example 1 above) using a loose-fitting Dounce homogenizer. By phase contrast microscopy, nuclei were free of cytoplasmic blebs. Nuclei were washed once in buffer A, resuspended in 3 ml of buffer A+0.1M KOAc and treated with a sonicator (Ultrasonics, Inc.) at a power setting of 7 for three 15-second bursts on ice. The sonicate was centrifuged at 16,000×g for 15 min to pellet debris. The supernatant was saved as the nuclear fraction. The post-nuclear supernatant described above was centrifuged at 20,000×g for 15 min. The pellet was washed once in buffer A, resuspended in 3 ml buffer A and saved as the mitochondrial fraction. The post-mitochondrial supernatant was layered on top of a cushion of 30% sucrose in buffer A and centrifuged at 130,000×g for 2.5 hr in a SW50.1 rotor. The supernatant above the pad was saved as the cytosol (S130) fraction. The pellet was washed twice with buffer A and resuspended in 0.3 ml of buffer A using a glass homogenizer and saved as the polysome fraction. The resulting nuclei, mitochondria, polysomes, and cytosol (S130) fractions were stored as small aliquots at −80° C. As shown in FIG. 5, equal cell equivalents (1×10$^6$ cells worth) of the indicated fractions were separated by SDS-PAGE on the same gel and analyzed by Western blotting using either a monoclonal antibody 4E4 (Wilusz and Shenk, Mol. Cell. Biol. 10:6397–6407 (1990)) which recognizes hnRNP A1/A2, B1/B2 and C1/C2 proteins (lanes 1–4) or affinity-purified α-p40 (lanes 5–8). The locations of the hnRNP A, B and C proteins and molecular weight markers (in kD) are indicated.

EXAMPLE 8

Screening of HeLa Expression Library and Analysis of Fusion Proteins

A HeLa λ ZAP II expression library was obtained from Dr. Barbara Yoza, Bowman Gray Sch. of Med., Winston-Salem, N.C. Recombinant plaques (600,000 total) were plated at a density of 30,000 pfu per 150 mm$^2$ plate of E. coli BB4. After incubation for 4 hr at 42° C., plates were overlaid with nitrocellulose filters soaked in 10 mM isopropyl β-D-thiogalactoside (IPTG) and incubated for 4 hr at 37° C. Replica filters soaked in IPTG were overlaid on the plates and incubated for another 6 hr at 37° C. Filters were blocked in BLOTTO (5% non-fat dry milk) then incubated for 2 hr. at room temperature with affinity-purified anti-p40 antibody (described above) diluted 1:50 in BLOTTO. Filters were washed in PBS and developed with $^{125}$I-labeled protein A (ICN). Plaques yielding duplicate positive signals were purified by several rounds of dilution and antibody screening until 100% of the plaques yielded positive signals.

Clones were subcloned into pBluescript by phage rescue. Cell lysates were prepared as described by Zapp and Green, Nature 342:714–716 (1989). Protein was analyzed by SDS-PAGE and Western blotting with α-p40 antibody, by UV-crosslinking and immunoprecipitation of crosslinked protein.

EXAMPLE 9

RNA-Binding Characterization of Fusion Proteins from cDNA Clones

Figure 6D:
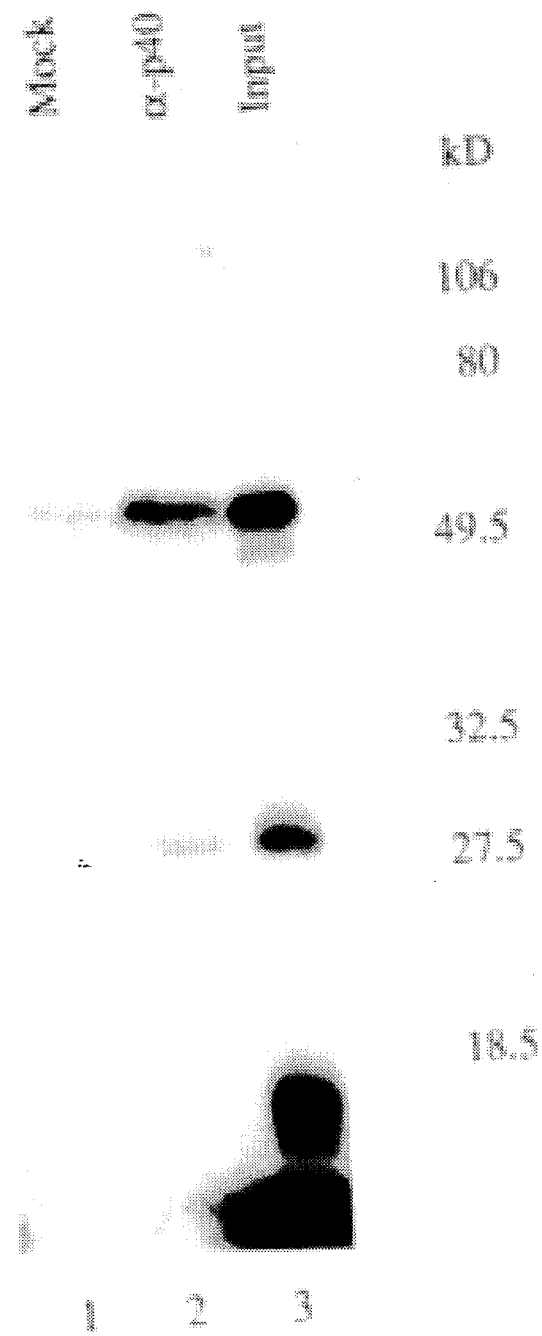
FIG. 6D represents a SDS-PAGE showing a UV-crosslinking of fusion protein pBS8 to $^{32}$P-labeled c-myc ARE and immunoprecipitation analysis.

UV-crosslinking analysis is represented by an SDS-PAGE in FIG. 6A. Lysates of bacteria containing either pBS8, pBS10 or phagemid vector were incubated with labeled c-myc ARE (lanes 3–5) or $^{32}$P-labeled β-globin 3'UTR (lanes 6–8) indicated above each lane. Reactions were irradiated with UV light and treated with RNase A as described in FIG. 2. Polypeptides were visualized by SDS-PAGE and autoradiography. Control reactions contained probes only (c-myc ARE, lane 1; β-globin 3'UTR, lane 2). In FIG. 6B is a SDS-PAGE showing UV-crosslinking competition analysis of ARE binding. $^{32}$P-labeled c-myc ARE was incubated with lysate from pBS8 cells and the indicated molar excess of either unlabeled c-myc ARE (lanes 2–5) or unlabeled β-globin 3'UTR (lanes 6–8). A control reaction contained c-myc ARE probe only (lane 1). Binding was assayed by UV-crosslinking as described in FIG. 2. In FIG. 6C is a graph showing the quantitation of RNA-binding activity. The 55 kD band in the autoradiographs of panel B were scanned by soft laser densitometry and plotted as percent binding (compared to no competitor) versus molar excess competitor indicated to the right of each curve. FIG. 6D represents an SDS-PAGE showing UV-crosslinking and immunoprecipitation analysis of fusion protein pBS8. $^{32}$P-labeled c-myc ARE was mixed with lysate from pBS8 and subjected to UV-crosslinking and RNase treatment. Mixtures were either not precipitated (lane 3) or immunoprecipitated with either mock pre-immune (lane 1) or anti-p40 antibody (lane 2). Proteins were visualized by SDS-PAGE and autoradiography. Molecular weights of markers are indicated for each panel.

EXAMPLE 10

In Vitro Translation of RNA from AUF1 cDNA Clone pBS8

The XbaI-XhoI fragment of the AUF1 cDNA clone pBS8 was cloned into a derivative of plasmid pGEM-7Zf(+) in which the SphI site in the polylinker was destroyed (to remove an ATG present in the multiple cloning site of plasmid pGEM-7Zf(+)). AUF1 mRNA was prepared by transcription of the XhoI-digested plasmid using T7 RNA polymerase. RNA was translated in rabbit reticulocyte lysate (Promega) supplemented with 1 mCi/ml Tran$^{35}$S-label (ICN) following the manufacturer's protocol except that compensation buffer (final concentration 42 mM KOAc, 0.75 mM Mg(OAc)$_2$, 15 mM TAE) was added. Translation products were fractionated by 10% SDS-PAGE and visualized by autoradiography.

For comparison, immunoprecipitation of proteins from a lysate of K562 cells metabolically labeled with $^{35}$S-methionine using α-p40 was also performed. Products were separated by 10% SDS-PAGE and visualized by autoradiography. In FIG. 7, the molecular weights in kD of marker proteins are shown at the right; the locations of the 37, 40 and 45 kD polypeptides in immunoprecipitates are shown at the left. Lanes: 1, immunoprecipitation of proteins from a lysate of K562 cells metabolically labeled with $^{35}$S-methionine using α-p40; 2, in vitro translation with AUF1 RNA synthesized in vitro using T7 RNA polymerase; 3, in vitro translation in the absence of added RNA.

EXAMPLE 11

Nucleotide Sequence Analysis and Predicted Amino Acid Sequence

Overlapping restriction fragments deduced from the restriction map were subcloned into pGEM-7Zf(+) or pGEM 3Z (Promega). In order to facilitate sequencing the 3'UTR, the 2.5 kb AUF1 cDNA insert was subcloned into the XbaI-XhoI sites of pGEM-7Zf(+). Nested deletions of cDNA inserts were prepared by digestion of linearized plasmids with exonuclease III and nuclease S1 (Promega), followed by closing the modified plasmids. Sequence across restriction sites used for subcloning and regions inaccessible by universal primer sequencing was obtained using synthetic oligonucleotides (Operon) and the original p37$^{AUF1}$ cDNA were merged and analyzed for functional motifs using the Wisconsin Genetics Computer Group software (Devereux et al., *Nuc. Acids Res.* 12:387–395 (1984)).

In FIGS. 8A, 8B, and 8C SEQ ID NO:4 is shown the nucleotide sequence of the cloned cDNA and the predicted amino acid sequence. The indicated amino acid sequence is the largest ORF within the cloned insert and is in frame with the 5'UTR, consistent with expression as a fusion protein in the λ ZAP vector. Nucleotides are numbered with +1 assigned as the first guanine residue in the EcoRI site of the inserted cDNA clone. FIG. 8D shows the Northern blot analysis of AUF1 mRNA. Five micrograms of poly(A+) RNA from K562 cells was analyzed by Northern blot assay as described (Brewer and Ross, *Mol. Cell. Biol.* 8:1697–1708 (1988)) using a $^{32}$P-labeled p37$^{AUF1}$ probe from the 3'UTR. The positions of 28S and 18S ribosomal RNAs are indicated. The 2.5 kb AUF1 mRNA is indicated by the arrow.

EXAMPLE 12

Analysis of RNA-Binding by an AUF1 Polypeptide Fragment

Figure 9:
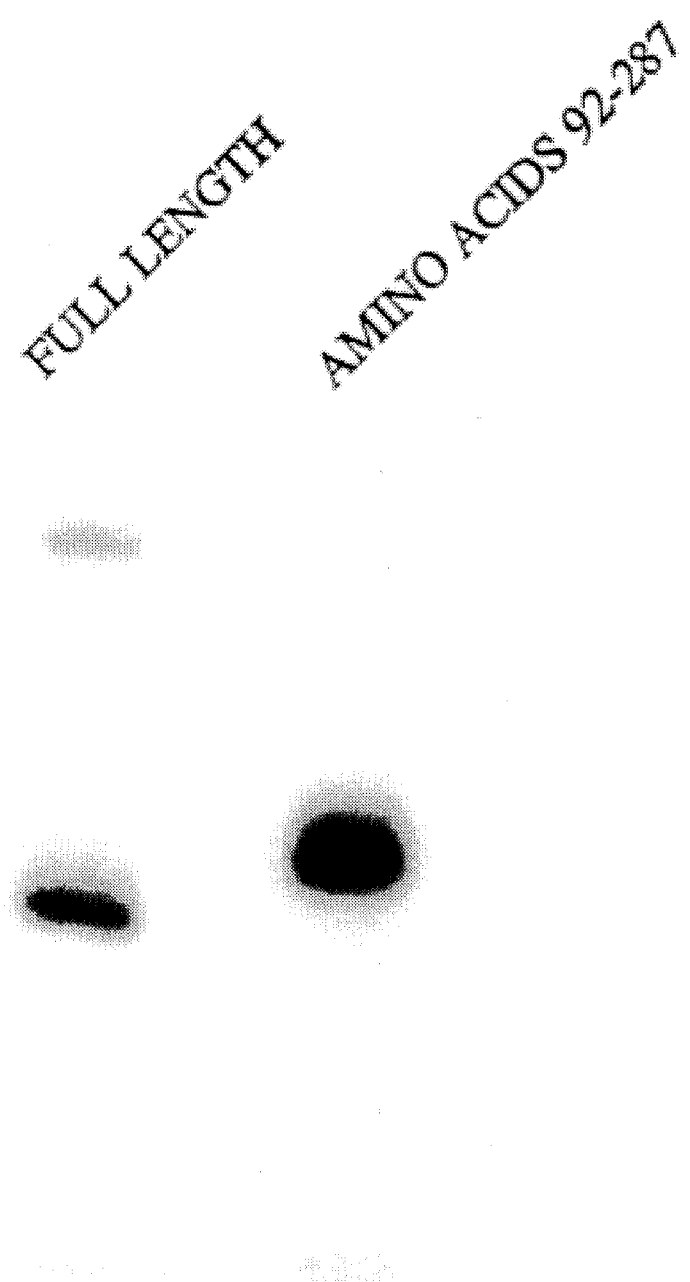
FIG. 9 represents an SDS-PAGE showing UV crosslinking analysis of AUF1 and AUF1 fragment to $^{32}$P-labeled c-myc ARE in the presence of excess unlabeled competitor RNAs.

An AUF1 polypeptide fragment containing amino acids 92–287 was constructed by subcloning a BglII-HindIII fragment of the AUF1 cDNA into a prokaryotic expression vector pTrcHis (Invitrogen Corp, San Diego, Calif.). This was introduced into bacteria and expressed. Bacteria with the full length AUF1 cDNA was used as a control. Lysates were prepared from each and used in a UV-crosslinking assay with the c-myc wild-type ARE substrate described in Example 4. The UV-crosslinking procedure was as described in Example 4. Crosslinking to the full length polypeptide is indicated by the arrow at the left of the panel in FIG. 9. The lower band in that lane is a proteolytic fragment generated during preparation of the lysate. Crosslinking to the polypeptide fragment AUF1 containing amino acids 92–287 is shown in the adjacent lane. This experiment demonstrates that the biological activity of AUF1 (i.e., the ARE-binding activity) is retained by a fragment of the full length polypeptide.

EXAMPLE 13

Treatment of Patients Having Low Levels of the AUF1 Gene

Polypeptide therapy can be given to those individuals determined to have low levels of the AUF1 gene, and who therefore are at risk of developing tumors.

To prevent the formation of tumors in these individuals, the AUF1 polypeptide is administered therapeutically in an amount sufficient to inhibit tumor formation or growth (anti-tumor forming amount). An anti-tumor-forming dosage of the AUF1 polypeptide is 1 to 500 µg/kilogram of body weight/day. The AUF1 polypeptide can be administered by injection with a pharmacologically acceptable carrier, either alone or in combination with another agent. Acceptable pharmacological carriers are those which dissolve the AUF1 polypeptide or hold it in suspension, and which are not toxic to the extent of permanently harming the patient. Preferred are aqueous solutions of salts or non-ionic compounds such as sodium chloride or glucose, more preferably at an isotonic concentration. Other agents may be present provided that they do not interfere with the action of the AUF1 polypeptide. Those skilled in the art will know, or will be able to ascertain with no more than routine experimentation, particular pharmacological carriers for this composition.

AUF1 polypeptide suitable for therapy can be prepared by any one of the following three conventional procedures. First, the AUF1 polypeptide can be produced by expressing the cDNA product from a procaryotic or eucaryotic expression vector, in an in vitro expression system, and purifying and isolating the AUF1 polypeptide from the medium or cells of the expression system. General expression vectors and systems are well known in the art.

Second, the AUF1 polypeptide can be produced using protein chemistry techniques, wherein the specific amino acid residues are joined together synthetically in the appropriate sequence.

Third, naturally occurring AUF1 protein can be isolated from total protein samples by affinity chromatography. Antibodies specific for the AUF1 protein are prepared by standard procedures (Harlow & Lane, Antibodies, *A Laboratory Manual*, Cold Spring Harbor Laboratory, N.Y. (1988)) and coupled to an inert matrix, which is then used to selectively bind the AUF1 proteins.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

What is claimed is:

1. A purified and isolated AUF1 polypeptide capable of limiting the expression of a proto-oncogene, wherein the amino acid sequence is coded for by a DNA sequence set out in SEQ ID NO:4.

2. A polypeptide fragment, of SEQ ID NO.: 4, capable of limiting the expression of a proto-oncogene, whose amino-terminal sequence begins with amino-terminal amino acid residue 92 Asp and whose carboxy-terminal residue extends no further than amino acid residue 287 Val.

3. An antibody produced to the polypeptide of claim 1.

4. The antibody of claim 3, wherein the antibody is a monoclonal antibody.

* * * * *